(12) United States Patent
Kangasmetsa et al.

(10) Patent No.: US 9,035,071 B2
(45) Date of Patent: May 19, 2015

(54) COMPOUNDS ACTING AT MULTIPLE PROSTAGLANDIN RECEPTORS GIVING A GENERAL ANTI-INFLAMMATORY RESPONSE

(71) Applicant: Allergan, Inc., Irvine, CA (US)

(72) Inventors: Jussi J. Kangasmetsa, Essex (GB); William R. Carling, Bishop's Stortford (GB); Jose L. Martos, Basildon Essex (GB); David F. Woodward, Lake Forest, CA (US); Jenny W. Wang, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 47 days.

(21) Appl. No.: 13/720,488

(22) Filed: Dec. 19, 2012

(65) Prior Publication Data

US 2013/0165666 A1 Jun. 27, 2013

Related U.S. Application Data

(60) Provisional application No. 61/580,474, filed on Dec. 27, 2011.

(51) Int. Cl.
*C07D 231/38* (2006.01)
*C07D 231/14* (2006.01)
*C07D 231/12* (2006.01)

(52) U.S. Cl.
CPC ............ *C07D 231/38* (2013.01); *C07D 231/12* (2013.01); *C07D 231/14* (2013.01)

(58) Field of Classification Search
None
See application file for complete search history.

(56) References Cited

U.S. PATENT DOCUMENTS

| | | | |
|---|---|---|---|
| 4,166,452 A | 9/1979 | Generales | |
| 4,256,108 A | 3/1981 | Theeuwes | |
| 4,265,874 A | 5/1981 | Bonsen | |
| 6,316,448 B1 | 11/2001 | Arnold | |
| 6,511,999 B2 | 1/2003 | Burk | |
| 8,492,424 B2 * | 7/2013 | Carling et al. | 514/406 |
| 2004/0162323 A1 | 8/2004 | Krauss | |
| 2005/0014813 A1 | 1/2005 | Tawada | |
| 2005/0065200 A1 | 3/2005 | Woodward | |
| 2007/0014054 A1 | 1/2007 | Zhang | |
| 2007/0060596 A1 | 3/2007 | Giblin | |

FOREIGN PATENT DOCUMENTS

| | | |
|---|---|---|
| EP | 2457900 | 5/2012 |
| WO | 2005-040128 | 5/2005 |
| WO | 2005-042534 | 5/2005 |
| WO | 2008-033455 | 3/2008 |
| WO | 2008-138876 | 11/2008 |
| WO | 2011-092140 | 8/2011 |
| WO | 2012-130633 | 10/2012 |

OTHER PUBLICATIONS

Castellani, ML et al, Anti-Chemokine Therapy for Inflammatory Diseases, International Journal of Immunopathology and Pharmacology, 2007, 447-453, 20(3), US.
Cecchi, L. et al, Synthesis and Biological Activity of Some 3-(Pyrazol-1'-yl) Indazole Derivatives, Retrieved from STN Database Accession No. 1985:21078, 1984, 1 Page, Database CA Chemical Abstracts Service.
Conti, P. et al, MCP-1 and RANTES Are Mediators of Acute and Chronic Inflammation, Allergy and Asthma Proc, 2001, 133-137, 22, US.
Fukushi, Hideto et al, Preparation of Heterocyclic Compounds as CaSR (Calcium-Sensing Receptor) Antagonists, Retrieved from STN Database Accession No. 2010:1373480, 2010, 1 Page, Database Chemical Abstracts Service.
Garcia, Gilles et al, New Chemokine Targets for Asthma Therapy, Current Allergy and Asthma Reports, 2005, 155-160, 5, US.
Gleissner, Christian A. et al, Platelet Chemokines in Vascular Disease, ATVB in Focus Chemokines in Atherosclerosis, Thrombosis, and Vascular Biology, 2008, 1920-1927, 28, US.
Ho, CY et al, Suppressive effect of combination treatment of leflunomide and methotrexate on chemokine expression in patients with rheumatoid arthritis, Clin Exp Immunol, 2003, 132-138, 133, US.
Iwamoto, Takuji et al, Molecular aspects of rheumatoid arthritis: chemokines in the joints of patients, The FEBS Journal, 2008, 4448-4455, 275, US.
Matias, I., Prostaglandin Ethanolamides (Prostamides): In Vitro Pharmacology and Metabolism, The Journal of Pharmacology and Experimental Therapeutics, Jan. 29, 2004, 745-757, 209(2), US.
McKeown, Stephen et al, Identification of Novel Pyrazole Acid Antagonists for the EP1 Receptor, Bioorganic & Medicinal Chemistry Letters, 2006, 4767-4771, 16.

(Continued)

*Primary Examiner* — Kamal Saeed
(74) *Attorney, Agent, or Firm* — Jonathan Y. Bass

(57) ABSTRACT

The present invention provides a compound that is represented by the following general formula

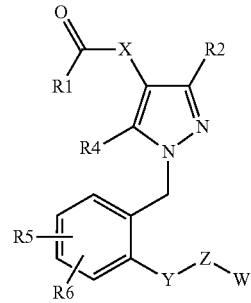

wherein $R_1$, $R_2$, $R_4$, $R_5$, $R_6$, $R_7$, X, W, X and Y are as defined in the specification. The compounds may be administered to treat DP1, FP, EP1, TP and/or EP4 receptor mediated diseases or conditions.

22 Claims, 3 Drawing Sheets

(56) References Cited

OTHER PUBLICATIONS

Figure 1:
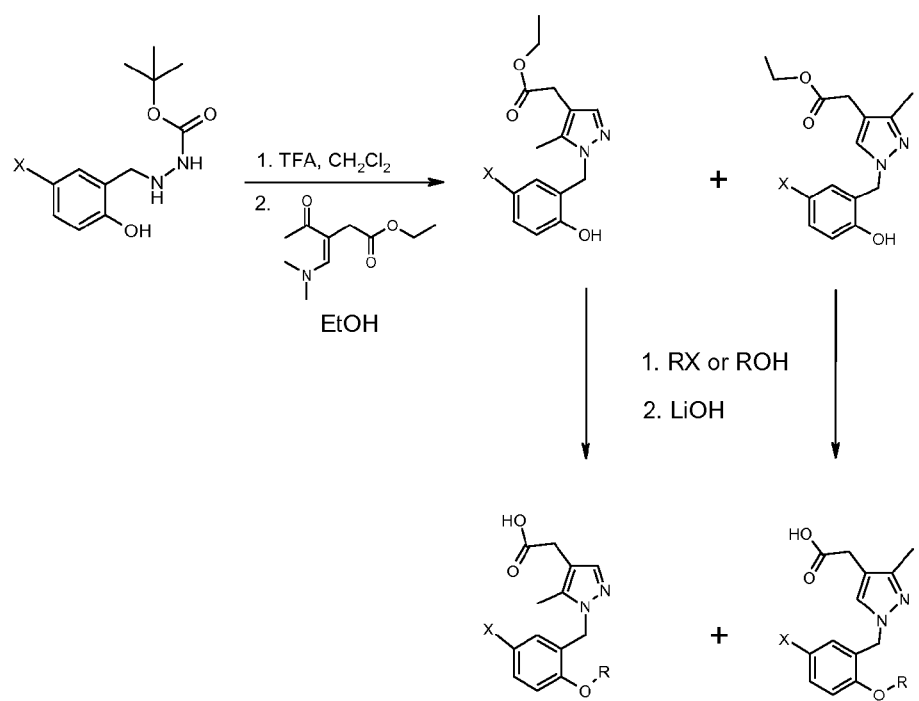

Pivarcsi, Andor et al, Chemokine Networks in Atopic Dermatitis: Traffic Signals of Disease, Current Allergy and Asthma Reports, 2005, 284-290, 5, US.

Qi, Xu-Feng et al, The adenylyl cyclase-cAMP system suppresses TARC/CCL17 and MDC/CCL22 production through p38 MAPK and NF-KB in HaCaT keratinocytes, Molecular Immunology, 2009, 1925-1934, 46, US.

Remingtons, Remingtons_16th, Pharmaceutical Sciences, 1980, 1-10, 16, Remingtons_16th.

Woodward, David et al, Characterization of Receptor Subtypes Involved in Prostanoid-Induced Conjunctival Pruritus and Their Role in Mediating Allergic Conjunctival Itching, The Journal of Pharmacology and Experimental Therapeutics, 1996, 137-142, 279.

Zernecke, Alma, Chemokines in Atherosclerosis an Update, Arterioscler Thromb Vasc Biol, 2008, 1897-1908, 28, US.

Patent Cooperation Treaty, Notification of Transmittal of the International Search Report and the Written Opinion of the International Searching Authority, or the Declaration, Form PCT/ISA/220, Int. App. No. PCT/US2012/070664, Mar. 19, 2013.

\* cited by examiner

COMPOUNDS ACTING AT MULTIPLE PROSTAGLANDIN RECEPTORS GIVING A GENERAL ANTI-INFLAMMATORY RESPONSE

CROSS-REFERENCE TO RELATED APPLICATION

This application claims the benefit of U.S. Provisional Application Ser. No. 61/580,474, filed Dec. 27, 2011, which is incorporated herein by reference in its entirety.

BACKGROUND OF THE INVENTION

1. Field of the Invention

This invention relates to compounds, to processes for their preparation, to pharmaceutical compositions containing them and to their use in medicine, in particular their use in the treatment of conditions mediated by the action of ligands for the $DP_1$, FP, TP, $EP_1$ and $EP_4$ prostaglandin (PG) receptors. The present compounds have the general structure shown below and act at different prostaglandin receptors to thereby provide a general anti-inflammatory response.

2. Summary of the Related Art

The $EP_1$ receptor is a 7-transmembrane receptor and its natural ligand is the prostaglandin $PGE_2$. $PGE_2$ also has affinity for the other EP receptors (types $EP_2$, $EP_3$ and $EP_4$). The $EP_1$ receptor is associated with smooth muscle contraction, pain (in particular inflammatory, neuropathic and visceral), inflammation, allergic activities, renal regulation and gastric or enteric mucus secretion.

Prostaglandin $E_2$ ($PGE_2$) exerts allodynia through the $EP_1$ receptor subtype and hyperalgesia through $EP_2$ and $EP_3$ receptors in the mouse spinal cord. Furthermore, it has been shown that in the $EP_1$ knock-out mouse pain-sensitivity responses are reduced by approximately 50%. $EP_1$ receptor antagonist (ONO-8711) reduces hyperalgesia and allodynia in a rat model of chronic constriction injury and inhibits mechanical hyperalgesia in a rodent model of post-operative pain. The efficacy of $EP_1$ receptor antagonists in the treatment of visceral pain in a human model of hypersensitivity has been demonstrated. Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects. Moreover, as a result of sparing potentially beneficial prostaglandin pathways, these agents may have enhanced efficacy over NSAIDS and/or COX-2 inhibitors. (See Pub. No. US 2005/0065200, which is hereby incorporated by reference, for other diseases that may be treated by EP4 receptor antagonists.)

The TP (also known as $TxA_2$) receptor is a prostanoid receptor subtype stimulated by the endogenous mediator thromboxane. Activation of this receptor results in various physiological actions primarily incurred by its platelet aggregatory and smooth muscle constricting effects, thus opposing those of prostacyclin receptor activation.

TP receptors have been identified in human kidneys in the glomerulus and extraglomerular vascular tissue. Activation of TP receptors constricts glomerular capillaries and suppresses glomerular filtration rates indicating that TP receptor antagonists could be useful for renal dysfunction in glomerulonephritis, diabetes mellitus and sepsis.

Activation of TP receptors induces bronchoconstriction, an increase in microvascular permeability, formation of mucosal edema and mucus secretion, which are typical characteristic features of bronchial asthma. TP antagonists have been investigated as potential asthma treatments resulting in, for example, orally active Seratrodast (AA-2414). Ramatroban is another TP receptor antagonist currently undergoing phase III clinical trials as an anti-asthmatic compound.

Since the $DP_1$ receptor may trigger an asthmatic response in certain individuals, compounds that have $DP_1$ antagonist properties may be useful as anti-asthmatic drugs. (See Pub. No. 2004/0162323 for the disclosure of other diseases and conditions that may be treated with DP antagonists.)

Finally, the FP receptor modulates intraocular pressure and mediates smooth muscle contraction of the sphincter muscles in the gastrointestinal tract and the uterus. Thus, antagonists of the FP receptor are useful for treating reproductive disorders. (See U.S. Pat. No. 6,511,999 for other diseases and conditions that may be treated with FP receptor antagonists.)

As further background for the present invention, see US Published Patent Application 2007/0060596 which is hereby incorporated by reference in its entirety.

BRIEF SUMMARY OF THE INVENTION

This invention provides a compound, that is a 1-[(5-halo or alkyl or fluoroalkyl or alkoxy-2-{(hydrocarbyl or substituted hydrocarbyl)oxy}phenyl)methyl]-(3 and/or 5-alkyl or fluoroalkyl)-1H-pyrazole-4-(carboxylic acid or methylene carboxylic acid) or an alkyl or aryl ester or sulfonamide thereof.

In the compound of this invention said halo may be selected from the group consisting of chloro and bromo and said hydrocarbyl may be selected from the group consisting of alkyl and carbocyclic aryl.

Preferably, said hydrocarbyl is selected from the group consisting of branched chain alkyl and phenyl and more preferably said hydrocarbyl is selected from the group consisting of branched chain alkyl having from 4 to 7 carbons.

The compound of this invention may be a 1-[(5-chloro or bromo- or trifluoromethyl-2-{hydrocarbyloxy}phenyl)methyl]-(3 and/or -5 methyl)-1H-pyrazole-4-carboxylic acid, wherein said hydrocarbyl is selected from the group consisting of alkyl and carbocyclic aryl and wherein said hydrocarbyl may be selected from the group consisting of branched chain alkyl and phenyl, e.g. a branched chain alkyl having from 4 to 7 carbons.

Most preferably, the compound of this invention is selected from the group consisting of:

1-[(5-Bromo-2-{2-ethylbutyloxy}phenyl)methyl]-5-methyl-1H-pyrazole-4-methylenecarboxylic acid;
1-[(5-Bromo-2-{2-ethylbutyloxy}phenyl)methyl]-5-methyl-1H-pyrazole-4-carboxylic acid;
1-[(5-Bromo-2-{2-ethylbutyloxy}phenyl)methyl]-3-methyl-1H-pyrazole-4-carboxylic acid;
1-[(5-chloro-2-{2-ethylbutyloxy}phenyl)methyl]-1H-pyrazole-4-carboxylic acid;
1-[(5-Chloro-2-{2-ethylbutyloxy}phenyl)methyl]-3,5-dimethyl-1H-pyrazole-4-carboxylic acid;
1-[(5-chloro-2-{2-ethylbutyloxy}phenyl)methyl]-3-propyl-1H-pyrazole-4-carboxylic acid;

1-[(5-chloro-2-{2-ethylbutyloxy}phenyl)methyl]-5-propyl-1H-pyrazole-4-carboxylic acid;
1-[(5-trifluoromethyl-2-{2-ethylbutyloxy}phenyl)methyl]-5-methyl-1H-pyrazole-4-carboxylic acid;
1-[(5-trifluoromethyl-2-{2-ethylbutyloxy}phenyl)methyl]-3-methyl-1H-pyrazole-4-carboxylic acid; and,
1-[(5-Chloro-2-{2-ethylbutyloxy}phenyl)methyl]-5-methyl-1H-pyrazole-4-carboxylic acid.

More preferably, the compound of this invention is selected from the group consisting of:
1-[(5-Bromo-2-{2-ethylbutyloxy}phenyl)methyl]-5-methyl-1H-pyrazole-4-methylenecarboxylic acid;
1-[(5-Bromo-2-{2-ethylbutyloxy}phenyl)methyl]-5-methyl-1H-pyrazole-4-carboxylic acid;
1-[(5-Bromo-2-{2-ethylbutyloxy}phenyl)methyl]-3-methyl-1H-pyrazole-4-carboxylic acid;
1-[(5-chloro-2-{2-ethylbutyloxy}phenyl)methyl]-1H-pyrazole-4-carboxylic acid;
1-[(5-Chloro-2-{2-ethylbutyloxy}phenyl)methyl]-3,5-dimethyl-1H-pyrazole-4-carboxylic acid;
1-[(5-chloro-2-{2-ethylbutyloxy}phenyl)methyl]-5-propyl-1H-pyrazole-4-carboxylic acid;
1-[(5-trifluoromethyl-2-{2-ethylbutyloxy}phenyl)methyl]-5-methyl-1H-pyrazole-4-carboxylic acid;
1-[(5-Chloro-2-{2-ethylbutyloxy}phenyl)methyl]-5-methyl-1H-pyrazole-4-carboxylic acid;
1-(5-chloro-2-isobutoxy-benzyl)-5-methyl-1h-pyrazole-4-carboxylic acid;
1-(5-chloro-2-cyclopentylmethoxy-benzyl)-5-methyl-1h-pyrazole-4-carboxylic acid;
1-(5-bromo-2-isobutoxy-benzyl)-5-methyl-1h-pyrazole-4-carboxylic acid;
1-[5-bromo-2-(2,2-dimethyl-propoxy)-benzyl]-5-methyl-1h-pyrazole-4-carboxylic acid;
1-[2-(2-ethyl-butoxy)-5-trifluoromethoxy-benzyl]-5-methyl-1h-pyrazole-4-carboxylic acid; and,
5-amino-1-[5-bromo-2-(2-ethyl-butoxy)-benzyl]-1h-pyrazole-4-carboxylic acid.

Most preferably, said compound is:
1-[(5-Bromo-2-{2-ethylbutyloxy}phenyl)methyl]-5-methyl-1H-pyrazole-4-methylenecarboxylic acid;
1-[(5-Bromo-2-{2-ethylbutyloxy}phenyl)methyl]-5-methyl-1H-pyrazole-4-carboxylic acid; or,
5-amino-1-[5-bromo-2-(2-ethyl-butoxy)-benzyl]-1h-pyrazole-4-carboxylic acid.

The invention further relates to pharmaceutical compositions containing the above compounds in combination with a pharmaceutically-acceptable excipient and to their use in medicine, in particular their use in the treatment of conditions mediated by the action of ligands for the $DP_1$, FP, $EP_1$ and $EP_4$ prostaglandin (PG) receptors. The compounds of this invention are also useful for treating conditions mediated by the action of ligands for the thromboxane (TP) receptor.

Some embodiments of the present invention include:
1. A compound, that is a 1-[(5-halo or alkyl or fluoroalkyl or alkoxy-2-{(hydrocarbyl or substituted hydrocarbyl)oxy}phenyl)methyl]-(3 or 5 alkyl or fluoroalkyl)-1H-pyrazole-4-(carboxylic acid or methylene carboxylic acid) or an alkyl or aryl ester or sulfonamide thereof. (As will be understood by those of ordinary skill in the art, certain compounds of the invention may be the same but have slightly different names. In one example, the compounds may be designated as a "methylene carboxylic acid" or an "acetic acid". They are the same, despite the different nomenclature.).
2. The compound of paragraph 1 wherein said halo is selected from the group consisting of chloro and bromo.
3. The compound of paragraph 1 wherein said hydrocarbyl is selected from the group consisting of alkyl and carbocyclic aryl.
4. The compound of paragraph 3 wherein said hydrocarbyl is selected from the group consisting of branched chain alkyl and phenyl.
5. The compound of paragraph 4 wherein said hydrocarbyl is selected from the group consisting of branched chain alkyl having from 4 to 7 carbons.
6. The compound of paragraph 1 wherein said compound is a 1-[(5-Chloro or bromo- or trifluoromethyl-2-{hydrocarbyloxy}phenyl)methyl]-(3 or 5 methyl)-1H-pyrazole-4-carboxylic acid.
7. The compound of paragraph 6 wherein said hydrocarbyl is selected from the group consisting of alkyl and carbocyclic aryl.
8. The compound of paragraph 6 wherein said hydrocarbyl is selected from the group consisting of branched chain alkyl and phenyl.
9. The compound of paragraph 6 wherein said hydrocarbyl a branched chain alkyl having from 4 to 7 carbons.
10. The compound of paragraph 1 that is selected from the group consisting of:
1-[(5-Bromo-2-{2-ethylbutyloxy}phenyl)methyl]-5-methyl-1H-pyrazole-4-methylenecarboxylic acid;
1-[(5-Bromo-2-{2-ethylbutyloxy}phenyl)methyl]-5-methyl-1H-pyrazole-4-carboxylic acid;
1-[(5-Bromo-2-{2-ethylbutyloxy}phenyl)methyl]-3-methyl-1H-pyrazole-4-carboxylic acid;
1-[(5-chloro-2-{2-ethylbutyloxy}phenyl)methyl]-1H-pyrazole-4-carboxylic acid;
1-[(5-Chloro-2-{2-ethylbutyloxy}phenyl)methyl]-3,5-dimethyl-1H-pyrazole-4-carboxylic acid;
1-[(5-chloro-2-{2-ethylbutyloxy}phenyl)methyl]-3-propyl-1H-pyrazole-4-carboxylic acid;
1-[(5-chloro-2-{2-ethylbutyloxy}phenyl)methyl]-5-propyl-1H-pyrazole-4-carboxylic acid;
1-[(5-trifluoromethyl-2-{2-ethylbutyloxy}phenyl)methyl]-5-methyl-1H-pyrazole-4-carboxylic acid;
1-[(5-trifluoromethyl-2-{2-ethylbutyloxy}phenyl)methyl]-3-methyl-1H-pyrazole-4-carboxylic acid; and,
1-[(5-Chloro-2-{2-ethylbutyloxy}phenyl)methyl]-5-methyl-1H-pyrazole-4-carboxylic acid.
11. A compound having the following formula:

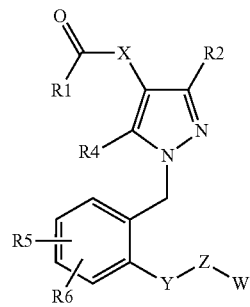

X is O, $NR_7$ or $(CH_2)_n$, wherein n is 0 or an integer of 1 or 2;
Y is $(CH_2)_m$, wherein m is 0 or an integer of from 1 to 3;
Z is selected from the group consisting of O, S, SO, $SO_2$ and $(CH_2)_p$, wherein p is 0 or an integer of from 1 to 3;
W is hydrocarbyl or substituted hydrocarbyl;
$R_1$ is selected from the group consisting of $OR_7$, $N(R_7)_2$, and $N(R_7)SO_2R_7$;

$R_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_4$ is selected from the group consisting of H, $NH_2$, alkyl, nitrogen substituted alkyl and halogen-substituted alkyl;

$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy; and, $R_7$ is selected from the group consisting of H, hydrocarbyl and substituted hydrocarbyl, e.g. carbocyclic aryl and alkyl.

12. The compound of paragraph 11, wherein $R_1$ is OH.

13. The compound of paragraph 11, wherein $R_2$ is selected from the group consisting of H, alkyl and halogen-substituted alkyl, e.g. fluoro-substituted alkyl.

14. The compound of paragraph 11, wherein $R_4$ is selected from the group consisting of H, alkyl and halogen-substituted alkyl, e.g. fluoro-substituted alkyl.

15. The compound of paragraph 11, wherein $R_1$ is X is $(CH_2)_n$, wherein n is 0 or 1.

16. The compound of paragraph 11, wherein $R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy.

17. The compound of paragraph 11, wherein $R_5$ is chloro or bromo.

18. The compound of paragraph 11, wherein $R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy.

19. The compound of paragraph 18, wherein $R_6$ is H.

20. The compound of paragraph 11, wherein Y is absent, i.e. n is 0.

21. The compound of paragraph 11, wherein Z is O.

22. The compound of paragraph 11, wherein W is selected from the group consisting of alkyl, aryl, alkoxy, aryloxy and hydroxy, halogen, nitro, amino and cyano-substituted alkyl, aryl, alkoxy or aryloxy.

23. The compound of paragraph 22, wherein W is selected from the group consisting of alkyl, e.g. branched chain alkyl such as 2-ethylbutyl, 2-methylpropyl, etc. and carbocyclic aryl, e.g. phenyl.

24. The compound of paragraph 11 that is selected from the group consisting of:

1-[(5-Bromo-2-{2-ethylbutyloxy}phenyl)methyl]-5-methyl-1H-pyrazole-4-methylenecarboxylic acid;

1-[(5-Bromo-2-{2-ethylbutyloxy}phenyl)methyl]-5-methyl-1H-pyrazole-4-carboxylic acid; and, 5-amino-1-[5-bromo-2-(2-ethyl-butoxy)-benzyl]-1h-pyrazole-4-carboxylic acid.

25. A method of making a {1-2-[(hydrocarbyl or substituted hydrocarbyloxy)-benzyl]1H-pyrazol- or alkyl-1H-pyrazol)-4-yl}-acetic or carboxylic acid which comprises hydrolyzing the corresponding {1-2-[(hydrocarbyl or substituted hydrocarbyloxy)-benzyl]1H-pyrazol-4-yl}-acetic or carboxylic acid, alkyl ester to yield said {1-2-[(hydrocarbyl or substituted hydrocarbyloxy)-benzyl]1H-pyrazol-4-yl}-acetic or carboxylic acid.

26. The method of paragraph 25 wherein said {1-2-[(hydrocarbyl or substituted hydrocarbyloxy)-benzyl]1H-pyrazol-4-yl}-acetic or carboxylic acid is a {1-[halo or haloalkyl-2-(hydrocarbyloxy)-benzyl]-alkyl-1H-pyrazol-4-yl}-acetic or carboxylic acid.

27. The method of paragraph 26 wherein said {1-[halo or haloalkyl-2-(hydrocarbyloxy)-benzyl]-alkyl-1H-pyrazol-4-yl}-acetic or carboxylic acid is a {1-[5-halo or haloalkyl-2-(branched chain alkyl or phenyloxy)-benzyl]-3 and/or 5-alkyl-1H-pyrazol-4-yl}-acetic or carboxylic acid.

28. The method of paragraph 27 wherein said halo or haloalkyl is selected from the group consisting of chloro, bromo and trifluoromethyl.

29. The method of paragraph 27 wherein said hydrocarbyl is a branched chain alkyl having from 4 to 7 carbons.

30. The method of paragraph 28 wherein said branched chain alkyl is 2-ethylbutyl.

31. The method of paragraph 27 wherein said 3 and/or 5 alkyl is selected from the group consisting of methyl and n-propyl.

32. The method of paragraph 25 wherein said {1-2-[(hydrocarbyl or substituted hydrocarbyloxy)-benzyl]1H-pyrazol- or alkyl-1H-pyrazol-4-yl}-acetic or carboxylic acid, alkyl ester is a {1-[5-bromo-2-(hydrocarbyloxy)-benzyl]-alkyl-1H-pyrazol-4-yl}-acetic or carboxylic acid, alkyl ester and said method further comprises the step of reacting a solution of the corresponding [1-(5-Bromo-2-hydroxy-benzyl)alkyl-1H-pyrazol-4-yl]-acetic or carboxylic acid alkyl ester with the corresponding hydrocarbyl alcohol to obtain said {1-[2-(hydrocarbyl oxy)-benzyl]-alkyl-1H-pyrazol-4-yl}-acetic or carboxylic acid, alkyl ester.

33. The method of paragraph 31 wherein said {1-[2-(hydrocarbyl oxy)-benzyl]1H-pyrazol- or alkyl-1H-pyrazol)-4-yl}-acetic or carboxylic acid, alkyl ester is a [1-(5-Bromo-2-hydroxy-benzyl)-5-methyl-1H-pyrazol-4-yl]-carboxylic or acetic acid ethyl ester and said method further comprises the steps of reacting a suspension of N'-(5-bromo-2-hydroxy-benzyl)-hydrazinecarboxylic acid tert-butyl ester with a mixture of $CH_2Cl_2$ and TFA and removing the volatiles therefrom to obtain a residue, dissolving said residue in absolute EtOH and adding a 3-[1-dimethylamino-methylidene]-oxoalkanoic acid ethyl ester to the resulting solution and obtaining a [1-(5-Bromo-2-hydroxy-benzyl)-5-methyl-1H-pyrazol-4-yl]-carboxylic or acetic acid ethyl ester.

34. The method of paragraph 32 wherein said 3-[1-dimethylamino-methylidene]-oxoalkanoic acid ethyl ester is 3-[1-dimethylamino-methylidene]-4-oxo-pentanoic acid ethyl ester to yield the acetic acid ethyl ester.

35. The method of paragraph 32 wherein said 3-[1-dimethylamino-methylidene]-oxoalkanoic acid ethyl ester is 2-[1-Dimethylamino-meth-(Z)-ylidene]-3-oxo-butyric acid methyl ester to yield the carboxylic acid ethyl ester.

36. The method of paragraph 25 wherein said {1-2-[(hydrocarbyl or substituted hydrocarbyloxy)-benzyl]1H-pyrazol- or alkyl-1H-pyrazol}-4-yl}-acetic or carboxylic acid, alkyl ester is a {1-[5-chloro-2-(hydrocarbyloxy)-benzyl]-(1H-pyrazol- or alkyl-1H-pyrazol)-4-yl}-acetic or carboxylic acid, alkyl ester and said method further comprises the steps of reacting a solution of a 4-pyrazole or an alkyl-4-pyrazole carboxylate with NaH, under an inert atmosphere, e.g. a $N_2$ atmosphere, contacting the resulting reaction product with a solution of methanesulfonic acid 5-chloro-2-(hydrocarbyloxy)-benzyl ester in a polar aprotic solvent, e.g. DMF, to obtain a 1-[5-Chloro-2-(hydrocarbyloxy)-benzyl]-(1H-pyrazol- or alkyl-1H-pyrazol)-4-acetic or carboxylic acid alkyl ester.

37. The method of paragraph 35 wherein said method further comprises the step of reacting a solution of [5-Chloro-2-(hydrocarbyloxy)-phenyl]-methanol, di-isopropyl-ethyl amine and methanesulfonic anhydride in CH$_2$Cl$_2$ to obtain said methanesulfonic acid 5-chloro-2-(hydrocarbyloxy)-benzyl ester.

38. The method of paragraph 36 wherein said method further comprises the step of reacting a solution of 5-Chloro-2-(hydrocarbyloxy)-benzaldehyde, MeOH and NaBH$_4$ under an inert atmosphere, e.g. N$_2$, to obtain said [5-Chloro-2-(hydrocarbyloxy)-phenyl]-methanol.

39. The method of paragraph 38 wherein said method further comprises the step of reacting a solution of 5-chloro-2-hydroxybenzaldehyde in a polar aprotic solvent, e.g. DMF, under an inert atmosphere, e.g. a N$_2$ atmosphere, at RT with 3-(chloromethyl)pentane, K$_2$CO$_3$, and tetrabutylammonium iodide to obtain 5-Chloro-2-(hydrocarbyloxy)-benzaldehyde.

40. The method of paragraph 35 wherein said pyrazol-4-yl is a 3 and/or 5 alkyl pyrazol-4-yl, e.g. a methyl or propyl pyrazol-4-yl.

41. The method of paragraph 25 wherein said {1-2-[(hydrocarbyl or substituted hydrocarbyloxy)-benzyl]1H-pyrazol- or alkyl-1H-pyrazol-4-yl}-acetic or carboxylic acid, alkyl ester is a {1-[5-trifluoromethyl-2-(hydrocarbyloxy)-benzyl]-alkyl-1H-pyrazol-4-yl}-acetic or carboxylic acid, alkyl ester and said method further comprises the step of reacting a solution of the corresponding [1-(5-trifluoromethyl-2-hydroxy-benzyl)alkyl-1H-pyrazol-4-yl]-acetic or carboxylic acid alkyl ester with the corresponding hydrocarbyl alcohol to obtain said {1-[5-trifluoromethyl-2-(hydrocarbyl oxy)-benzyl]-alkyl-1H-pyrazol-4-yl}-acetic or carboxylic acid, alkyl ester.

42. The method of paragraph 41 further comprising the steps of providing a solution of 1-(5-Methoxy-2-trifluoromethyl-benzyl)-5-methyl-1H-pyrazole-4-carboxylic acid ethyl ester in dry DCM, at 0° C., under an inert atmosphere, e.g. a N$_2$ atmosphere, a boron tribromide allowing the solution to warm to room temperature, quenching the solution with MeOH and refluxing to yield 1-(5-Trifluoromethyl-2-hydroxy-benzyl)-methyl-1H-pyrazol-4-yl carboxylic acid methyl ester.

43. The method of paragraph 42 further comprising the steps of providing a solution of ethyl-4-pyrazole carboxylate in a polar aprotic solvent, e.g. DMF, under an inert atmosphere, e.g. a N$_2$ atmosphere, at RT, and sequentially adding to said solution, NaH in mineral oil and a solution of bromomethyl substituted benzyl5-chloro-2-(2-ethyl-butoxy)-benzyl ester in a polar aprotic solvent, e.g. DMF, pouring the resulting solution into water, removing the volatiles and purifying the resulting crude product to yield 1-[5-Trifluoromethyl-2-(2-ethyl-butoxy)-benzyl]-1H-pyrazole-4-carboxylic acid ethyl ester as a 3:2 mixture with its regioisomer.

44. A method comprising administering a compound having the following formula:

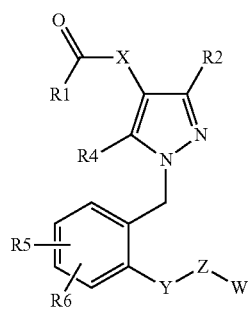

Wherein X is O, NR$_5$ or (CH$_2$)$_n$, wherein n is 0 or an integer of 1 or 2;

Y is (CH$_2$)$_m$, wherein m is 0 or an integer of from 1 to 3;

Z is selected from the group consisting of O, S, SO, SO$_2$ and (CH$_2$)$_p$, wherein p is 0 or an integer of from 1 to 3;

W is hydrocarbyl or substituted hydrocarbyl;

R$_1$ is selected from the group consisting of OR$_7$, N(R$_7$)$_2$, and N(R$_7$)SO$_2$R$_7$;

R$_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

R$_4$ is selected from the group consisting of H, NH$_2$, alkyl, nitrogen-substituted alkyl and halogen-substituted alkyl;

R$_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

R$_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy; and, R$_7$ is selected from the group consisting of H, hydrocarbyl and substituted hydrocarbyl, e.g. carbocyclic aryl and alkyl.

45. The method of paragraph 44 wherein said compound is administered to treat DP1, FP, EP1, TP and/or EP4 receptor mediated diseases or conditions.

46. The method of paragraph 45 wherein said condition or disease is related to inflammation.

47. The method of paragraph 45 wherein said DP1, FP, EP1, TP and/or EP4 receptor mediated condition or disease is selected from the group consisting of allergic conditions, asthma, allergic asthma, allergic rhinitis, uveitis and related disorders, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anticoagulation, diseases requiring control of bone formation and resorption, fertility disorders, gangrene, glaucoma, hyperpyrexia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, rheumatoid arthritis, pain, perennial rhinitis, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders.

48. The method of paragraph 45 wherein said compound is administered as a surgical adjunct in ophthalmology for cataract removal and artificial lens insertion, ocular implant procedures, photorefractive radial keratotomy and other ophthalmogical laser procedures.

49. The method of paragraph 45 wherein said compound is administered as a surgical adjunct in a procedure involving skin incisions, relief of pain and inflammation and scar formation/keloids post-surgery, for treating sports injuries and general aches and pains in muscles and joints.

50. The method of paragraph 45 wherein said DP$_1$, FP, EP$_1$, TP, and/or EP$_4$ receptor mediated condition or disease is an EP$_1$ and/or EP$_4$ receptor mediated condition or disease.

51. The method of paragraph 42 wherein said DP$_1$, FP, EP$_1$, TP and/or EP$_4$ receptor mediated condition or disease is an allergic condition.

52. The method of paragraph 51 wherein said condition is dermatological allergy.

53. The method of paragraph 51 wherein said condition is an ocular allergy.

54. The method of paragraph 51 wherein said condition is a respiratory allergy.

55. The method of paragraph 45 wherein said condition or disease is selected from the group consisting of nasal congestion, rhinitis, and asthma.

56. The method of paragraph 45 wherein said condition or disease is related to pain.

57. The method of paragraph 45 wherein said condition or disease is selected from the group consisting of arthritis, migraine, and headache.

58. The method of paragraph 45 wherein said condition or disease is associated with the gastrointestinal tract.

59. The method of paragraph 45 wherein said condition or disease is selected from the group consisting of peptic ulcer, heartburn, reflux esophagitis, erosive esophagitis, non-ulcer dyspepsia, infection by *Helicobacter pylori*, alrynitis, and irritable bowel syndrome.

60. The method of paragraph 56 wherein said condition or disease is selected from the group consisting of hyperalgesia and allodynia.

61. The method of paragraph 45 wherein said condition or disease is related to mucus secretion.

62. The method of paragraph 45 wherein said mucus secretion is gastrointestinal.

63. The method of paragraph 45 wherein said mucus secretion occurs in the nose, sinuses, throat, or lungs.

64. The method of paragraph 45 wherein said condition or disease is related to abdominal cramping.

65. The method of paragraph 45 wherein said condition or disease is irritable bowel syndrome.

66. The method of paragraph 45 wherein said condition or disease is a bleeding disorder.

67. The method of paragraph 45 wherein said condition or disease is a sleep disorder.

68. The method of paragraph 45 wherein said condition or disease is mastocytosis.

69. The method of paragraph 45 wherein said condition or disease is associated with elevated body temperature.

70. The method of paragraph 45 wherein said condition or disease is associated with ocular hypertension and glaucoma.

71. The method of paragraph 45 wherein said condition or disease is associated with ocular hypotension.

72. The method of paragraph 45 wherein said condition relates to surgical procedure to treat pain, inflammation and other unwanted sequalae wherein said surgical procedure includes incision, laser surgery or implantation.

73. The method of paragraph 45 where said condition is related to pain and inflammation and post-surgical scar and keloid formation.

74. A pharmaceutical product comprising a compound having the following formula:

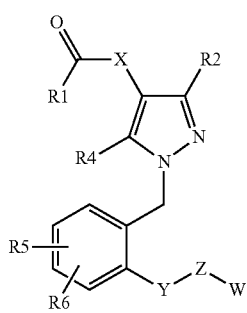

Wherein X is O, $NR_5$ or $(CH_2)_n$, wherein n is 0 or an integer of 1 or 2;

Y is $(CH_2)_m$, wherein m is 0 or an integer of from 1 to 3;

Z is selected from the group consisting of O, S, SO, $SO_2$ and $(CH_2)_p$, wherein p is 0 or an integer of from 1 to 3;

W is hydrocarbyl or substituted hydrocarbyl;

$R_1$ is selected from the group consisting of $OR_7$, $N(R_7)_2$, and $N(R_7)SO_2R_7$;

$R_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_4$ is selected from the group consisting of H, $NH_2$, alkyl, nitrogen-substituted alkyl and halogen-substituted alkyl;

$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy; and, $R_7$ is selected from the group consisting of H, hydrocarbyl and substituted hydrocarbyl, e.g. carbocyclic aryl and alkyl or a pharmaceutically acceptable salt or a prodrug thereof, wherein said product is packaged and labeled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, hyperpyrexia, gangrene, glaucoma, hypothermia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pain, perennial rhinitis, pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation.

75. A pharmaceutical composition comprising a compound having the following formula:

wherein X is O, $NR_5$ or $(CH_2)_n$, wherein n is 0 or an integer of 1 or 2;

Y is $(CH_2)_m$, wherein m is 0 or an integer of from 1 to 3;

Z is selected from the group consisting of O, S, SO, $SO_2$ and $(CH_2)_p$, wherein p is 0 or an integer of from 1 to 3;

W is hydrocarbyl or substituted hydrocarbyl;

$R_1$ is selected from the group consisting of $OR_7$, $N(R_7)_2$, and $N(R_7)SO_2R_7$;

$R_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_4$ is selected from the group consisting of H, $NH_2$, alkyl, nitrogen-substituted alkyl and halogen-substituted alkyl;

$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy; and, $R_7$ is selected from the group consisting of H, hydrocarbyl and substituted hydrocarbyl, e.g. carbocyclic aryl and alkyl or a pharmaceutically acceptable salt or a prodrug thereof, and a pharmaceutically acceptable excipient.

BRIEF DESCRIPTION OF THE DRAWING FIGURES

Figure 2:
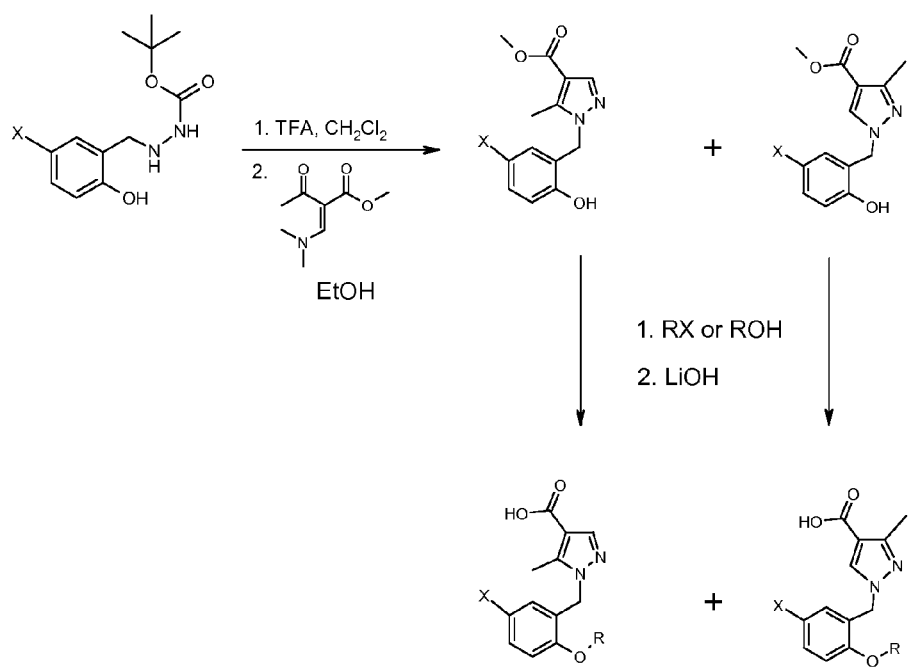
Figure 3:
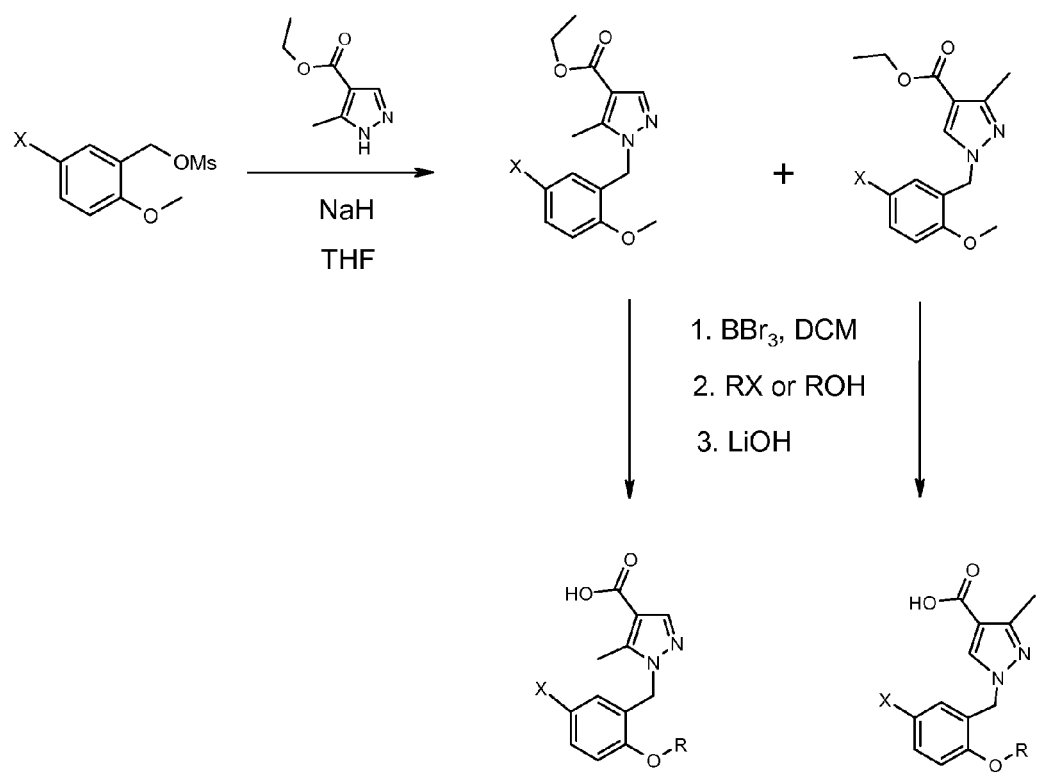

FIGS. 1, 2 and 3 show the reaction schemes for the preparation of the compounds of this invention.

DETAILED DESCRIPTION OF THE INVENTION

The following terms are used to define the disclosed invention.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Methylenyl" refers to a —$CH_2$— linking group. "Alkyl" refers to a straight-chain, branched or cyclic saturated aliphatic hydrocarbon. Preferably, the alkyl group has 1 to 12 carbons. More preferably, it is an alkyl of from 4 to 10 carbons, most preferably 4 to 8 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Cycloalkyl" refers to a cyclic saturated aliphatic hydrocarbon group. Preferably, the cycloalkyl group has 3 to 12 carbons. More preferably, it has from 4 to 7 carbons, most preferably 5 or 6 carbons.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of alkyl, hydroxyl, halogen, $COOR^7$, $NO_2$, $CF_3$, $N(R^7)_2$, $CON(R^7)_2$, $SR^7$, sulfoxy, sulfone, CN and $OR^7$, wherein $R^7$ is selected from the group consisting of H, hydrocarbyl and substituted hydrocarbyl, e.g. carbocyclic aryl and alkyl "Carbocyclic aryl" refers to an aryl group wherein the ring atoms are carbon.

"Heteroaryl or heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like. Preferably, the heteroaryl group has from 2 to 10 carbons. More preferably, it has from 3 to 10 carbons, most preferably 3 carbons.

Pharmaceutical compositions contemplated herein include compositions wherein the active ingredient is contained in an effective amount, i.e., in an amount effective to achieve its intended purpose. An "effective amount" is an amount sufficient to accomplish a stated purpose (e.g., achieve the effect for which it is administered, treat a disease, reduce one or more symptoms of a disease or condition). An example of an "effective amount" is an amount sufficient to contribute to the treatment, prevention, or reduction of a symptom or symptoms of a disease, which can be referred to as a "therapeutically effective amount." A "reduction" of a symptom or symptoms (and grammatical equivalents of this phrase) means decreasing of the severity or frequency of the symptom(s), or elimination of the symptom(s). The actual amount effective for a particular application will depend, inter alia, on the condition being treated.

"Treatment", "treat" or "treating" can refer to curing any disease or condition or reducing or alleviating the symptoms of the disease or condition.

The present invention provides compounds having the general formula:

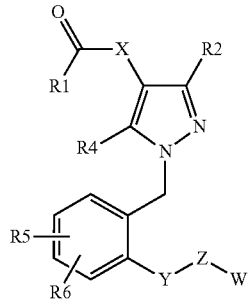

Wherein X is O, $NR_7$ or $(CH_2)_n$, wherein n is 0 or an integer of 1 or 2;

Y is $(CH_2)_m$, wherein m is 0 or an integer of from 1 to 3;

Z is selected from the group consisting of O, S, SO, $SO_2$ and $(CH_2)_p$, wherein p is 0 or an integer of from 1 to 3;

W is hydrocarbyl or substituted hydrocarbyl;

$R_1$ is selected from the group consisting of $OR_7$, $N(R_7)_2$, and $N(R_7)SO_2R_7$;

$R_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_4$ is selected from the group consisting of H, $NH_2$, alkyl, nitrogen-substituted alkyl and halogen-substituted alkyl;

$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_7$ is selected from the group consisting of H, hydrocarbyl and substituted hydrocarbyl, e.g. carbocyclic aryl and alkyl;

Preferably, $R_1$ is OH;

Preferably, $R_2$ is selected from the group consisting of H, alkyl and halogen-substituted alkyl, e.g. fluoro-substituted alkyl;

Preferably, R4 is selected from the group consisting of H, alkyl and halogen-substituted alkyl, e.g. fluoro-substituted alkyl;

Preferably, X is $(CH_2)n$, wherein n is 0 or 1;

Preferably, $R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy. More preferably $R_5$ is chloro or bromo;

Preferably, $R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy. More preferably $R_6$ is H;

Preferably, Y is absent, i.e. n is 0;

Preferably, Z is O;

Preferably, W is selected from the group consisting of alkyl, aryl, alkoxy, aryloxy and hydroxy, halogen, nitro, amino and cyano-substituted alkyl, aryl, alkoxy or aryloxy.

More preferably, W is selected from the group consisting of alkyl, e.g. branched chain alkyl such as 2-ethylbutyl, 2-methylpropyl, etc. and carbocyclic aryl, e.g. phenyl.

As shown in the Examples, below, preferably, certain of the preferred compounds of the present invention are prepared by a method of making a 1-[(hydrocarbyloxy)-benzyl]-1H-pyrazole-4-carboxylic acid which comprises the steps of:

(1) adding a reducing agent, e.g. NaH in mineral oil, to a solution of alkyl-4-pyrazole carboxylate dissolved in a polar aprotic solvent, e.g. DMF, under an inert atmosphere and stirring at RT;

(2) adding to the resulting mixture of step(1), a solution of methanesulfonic acid 2-(hydrocarbyl)-benzyl ester in a polar aprotic solvent, e.g. DMF, and stirring the resulting mixture for a sufficient time, e.g. 16 hours, to yield a reaction product comprising a 1-[2-(hydrocarbyl)-benzyl]-1H-pyrazole-4-carboxylic acid alkyl ester; and, (3) hydrolyzing the reaction product of step(2) comprising said 1-[2-(hydrocarbyl)-benzyl]-1H-pyrazole-4-carboxylic acid alkyl ester; and recovering a 1-[2-(hydrocarbyl)-benzyl]-1H-pyrazole-4-carboxylic acid.

An example of the above preferred method of making the preferred compounds, as shown in Example 4, below, is a method of making 1-[5-chloro-2-(2-ethyl-butoxy)-benzyl]-1H-pyrazole-4-carboxylic acid which comprises the steps of:

(1) adding NaH in mineral oil to a solution of ethyl-4-pyrazole carboxylate dissolved in a polar aprotic solvent under an inert atmosphere at RT and stirring;

(2) adding to the resulting mixture of step(1), a solution of methanesulfonic acid 5-chloro-2-(2-ethyl-butoxy)-benzyl ester dissolved in a polar aprotic solvent and stirring the resulting mixture at conditions sufficient to yield 1-[5-Chloro-2-(2-ethyl-butoxy)-benzyl]-1H-pyrazole-4-carboxylic acid ethyl ester;

(3) hydrolyzing the reaction product of step(2) to obtain 1-[5-chloro-2-(2-ethyl-butoxy)-benzyl]-1H-pyrazole-4-carboxylic acid; and, (4) recovering 1-[-2-(hydrocarbyl)-benzyl]-1H-pyrazole-4-carboxylic acid.

Said 5-chloro-2-(2-ethyl-butoxy)-phenyl]-methanol may be obtained by cooling a solution of 5-Chloro-2-(2-ethyl-butoxy)-benzaldehyde in MeOH to +5° C. under an inert atmosphere and adding NaBH and allowing the resulting mixture to warm to RT over 2 hours.

Said 5-Chloro-2-(2-ethyl-butoxy)-benzaldehyde, 10 may be obtained by adding a solution of 3-(chloromethyl)pentane, $K_2CO$ and tetrabutylammonium iodide in a polar aprotic solvent to a solution of 5-chloro-2-hydroxybenzaldehyde in a polar aprotic solvent under an inert atmosphere at RT and stirring the resulting mixture at 120° C. for a time sufficient to a obtain a reaction product comprising 5-Chloro-2-(2-ethyl-butoxy)-benzaldehyde.

Methanesulfonic acid 5-chloro-2-(2-ethyl-butoxy)-benzyl ester may be obtained by reacting a solution of [5-Chloro-2-(2-ethyl-butoxy)-phenyl]-methanol 11, di-isopropyl-ethyl amine and methanesulfonic anhydride under an inert atmosphere at conditions sufficient to yield said methanesulfonic acid 5-chloro-2-(2-ethyl-butoxy)-benzyl ester.

The corresponding bromo compound is prepared in Example 2 by an analogous method.

Said polar aprotic solvent may be selected from the group consisting of dichloromethane, tetrahydrofurane, ethylacetate, acetone, dimethylformamide, and acetonitrile.

The following examples are intended to illustrate the present invention.

The reagents and conditions used in FIGS. 1, 2, 3 and the Examples may be abbreviated as follows:

Ac is acetyl;

DCM is dichloromethane;

RT is room temperature;

Ph is phenyl;

DMF is dimethylformamide;

Et is ethyl;

THF is tetrahydrofuran; and,

HEPES is 4-(2-hydroxyethyl)-1-piperazineethanesulfonic acid).

Example 1

{1-[5-bromo-2-(2-ethyl-butoxy)-benzyl]-5-methyl-1H-pyrazol-4-yl}-acetic acid, 4

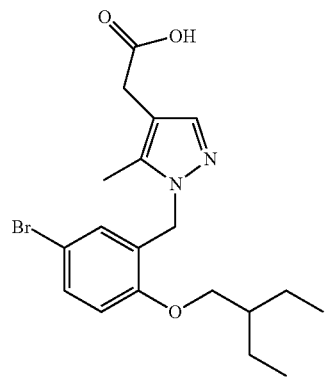 [SMILES: CCC(CC)COc1ccc(Br)cc1Cn1ncc(CC(=O)O)c1C]

Step 1

N'-(5-bromo-2-hydroxy-benzyl)-hydrazinecarboxylic acid tert-butyl ester 1

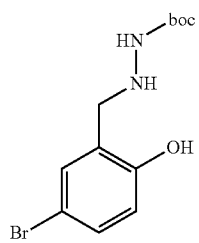

A solution of 5-bromo-2-hydroxybenzaldehyde (10 g g 50 mmol), tert-butylcarbazate (6.7 g, 52 mmol) and acetic acid (3 mL, 52 mmol) in $CH_2Cl_2$ (200 mL) was stirred under $N_2$ atmosphere for 60 min at RT. Then sodium triacetoxyborohydride (34 g, 159 mmol) was added portion wise and the resulting mixture was stirred at RT overnight. The reaction was quenched with 2 M HCl (100 mL) and stirred at RT for 1 h. The reaction mixture was partitioned between water (100 mL) and $CH_2Cl_2$ (250 mL). The organic layer was washed with sat. $NaHCO_3$ and brine (100 mL each), dried ($MgSO_4$) and evaporated to dryness to give hydrazine 1 as a white solid, 13 g (82%).

$^1$H-NMR ($CDCl_3$, 300 MHz) δ7.29 (dd, H ArH, J=2.4, 8.6 Hz), 7.17 (d, 1H, J=2.4 Hz, ArH), 6.80 (d, 1H, J=8.6 Hz, ArH), 1.49 (s, 9H, —$C(CH_3)_3$).

LC-MS: m/z 318 M+H$^+$

Step 2

[1-(5-Bromo-2-hydroxy-benzyl)-5-methyl-1H-pyrazol-4-yl]acetic acid ethyl ester, 2

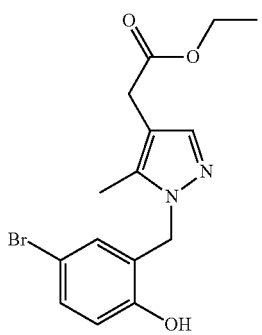 [SMILES: CCOC(=O)Cc1cnn(Cc2cc(Br)ccc2O)c1C]

A suspension of N'-(5-bromo-2-hydroxy-benzyl)-hydrazinecarboxylic acid tert-butyl ester 1 1 g (3.1 mmol) in a mixture of $CH_2Cl_2$ (8 mL) and TFA (8 mL) was stirred at RT for 2 hours. The volatiles were removed in vacuo. The residue was dissolved in abs. EtOH (7 mL) and added to 3-[1-dimethylamino-methylidene]-4-oxo-pentanoic acid ethyl ester (4.8 mmol) at RT. The resulting mixture was stirred at RT for 1 hour, refluxed for 2 h, let cool down and stirred at RT for 16 h. The oily residue obtained after removing the volatiles in vacuo was purified by MPLC (10 g $SiO_2$ cartridge, eluent 90% iso-hexane-10% EtOAc) to give 0.18 g of [1-(5-Bromo-2-hydroxy-benzyl)-5-methyl-1H-pyrazol-4-yl]-acetic acid ethyl ester, 2.

$^1$H-NMR ($CDCl_3$, 300 MHz) δ 7.45 (s, 1H, ArH), 7.33 (dd, 1H, ArH), 7727 (dd, 1H, ArH), 6.87 (dd, 1H, ArH), 5.11 (s, 2H, Ar$CH_2$), 4.16 (q, 2H, —$CH_2CH_3$), 3.39 (s, 2H, Ar$CH_2$), 2.34 (s, 3H, $CH_3$) 1.27 (t, 3H, —$CH_2CH_3$).

LC-MS: m/z 354 M+H$^+$

Step 3

{1-[5-Bromo-2-(2-ethyl-butoxy)-benzyl]-5-methyl-1H-pyrazol-4-yl}-acetic acid ethyl ester, 3

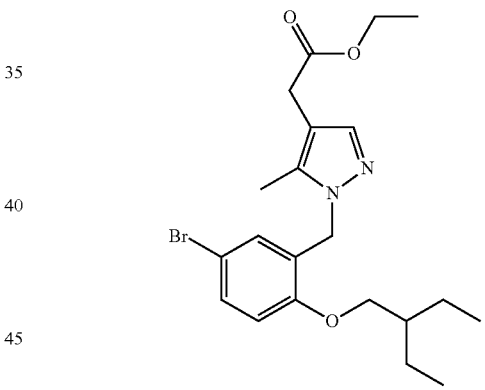

A solution of [1-(5-Bromo-2-hydroxy-benzyl)-5-methyl-1H-pyrazol-4-yl]-acetic acid ethyl ester, 2, (0.18 g g 0.51 mmol), triphenylphosphine (0.26 g, 1.02 mmol), di-tert-butylazodicarboxylate (0.23 g, 1.02 mmol) and 2-ethylbutan-1-ol (0.116 ml, 1.02 mmol) in a mixture of THF (1 mL) and toluene (2 ml) was at 120° C. on microwave for 20 min. The volatiles were removed in vacuo. The crude product was purified on silica to yield {1-[5-bromo-2-(2-ethyl-butoxy)-benzyl]-5-methyl-1H-pyrazol-4-yl}-acetic acid ethyl ester, 3.

a pale yellow oil, 0.1 g (45%).

$^1$H-NMR ($CDCl_3$, 300 MHz) δ 7.49 (s, 1H, ArH), 7.32 (dd, 1H ArH), 6.76 (4, 1H, ArH), 6.65 (dd, 1H, ArH), 5.27 (s, 2H, Ar$CH_2$), 4.17 (q, 2H, —$CH_2CH_3$), 3.90 (dd, 2H, $CH_2$), 3.45 (s, 2H, Ar$CH_2$),), 2.16 (s, 3H, $CH_3$), 1.71 (m, 1H, CH), 1.50 (m, 4H, $CH_2$), 1.28 (t, 3H, —$CH_2CH_3$), 0.96 (t, 6H, $CH_3$).

LC-MS: m/z 438 M+H$^+$

Step 4

{1-[5-Bromo-2-(2-ethyl-butoxy)-benzyl]-5-methyl-1H-pyrazol-4-yl}-acetic acid, 4

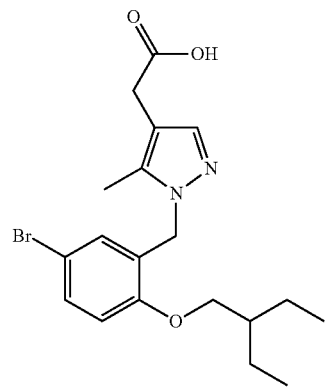 [SMILES: CCC(CC)COc1ccc(Br)cc1Cn1ncc(CC(=O)O)c1C]

To a solution of {1-[5-bromo-2-(2-ethyl-butoxy)-benzyl]-5-methyl-1H-pyrazol-4-yl}-acetic acid ethyl ester, 3, 0.1 g (0.22 mmol) in a mixture of THF (1 mL) and methanol (0.5 ml) was added a solution of LiOH (0.12 g in 1 ml H$_2$O). The resulting mixture was heated at 100° C. on microwave for 20 minutes. The mixture was poured into water (20 mL) and extracted with EtOAc (3×15 mL). The organic layers were combined, washed with brine (30 mL), dried (MgSO$_4$) and the volatiles removed in vacuo. The crude product was purified on silica to yield 7.4 mg (10%) of {1-[5-Bromo-2-(2-ethyl-butoxy)-benzyl]-5-methyl-1H-pyrazol-4-yl}-acetic acid, 4 as a white solid.

$^1$H-NMR (CDCl$_3$, 300 MHz) δ 7.50 (, 1H, ArH), 7.32 (dd, 1H, ArH), 6.76 (d, 1H ArH), 6.70 (dd, 1H, ArH), 5.27 (s, 2H, ArCH$_2$), 3.90 (dd, 2H, CH$_2$), 3.50 (s, 2H, ArCH$_2$), 2.16 (s, 3H, CH$_3$), 1.70 (m, 1H, CH), 1.50 (m, 4H, CH$_2$), 0.96 (t, 6H, CH$_3$).

LC-MS: m/z 410 M+H$^+$

Example 2

1-[5-bromo-2-(2-ethyl-butoxy)-benzyl]-5-methyl-1H-pyrazole-4-carboxylic acid, 7

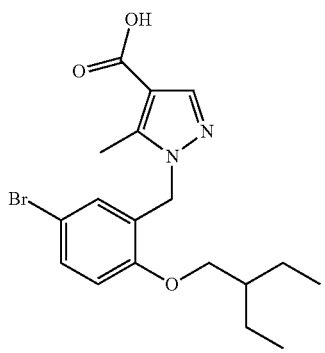

Step 1

1-(5-Bromo-2-hydroxy-benzyl)-5-methyl-1H-pyrazole-4-carboxylic acid methyl ester, 5

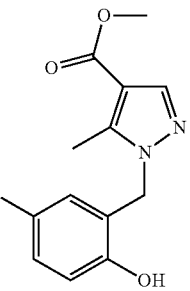

A suspension of N'-(5-bromo-2-hydroxy-benzyl)-hydrazinecarboxylic acid tert-butyl ester 1 2 g (6.3 mmol) in a mixture of CH$_2$Cl$_2$ (8 mL) and TFA (8 mL) was stirred at RT for 2 hours. The volatiles were removed in vacuo. The residue was dissolved in abs. EtOH (7 mL) and added to 2-[1-Dimethylamino-meth-(Z)-ylidene]-3-oxo-butyric acid methyl ester (12 mmol) at RT. The resulting mixture was stirred at RT for 1 hour, refluxed for 2 h, let cool down and stirred at RT for 16 h. The oily residue obtained after removing the volatiles in vacuo was purified by MPLC (10 g SiO$_2$ cartridge, eluent 90% iso-hexane-10% EtOAc) to give 0.38 g of 1-(5-Bromo-2-hydroxy-benzyl)-5-methyl-1H-pyrazole-4-carboxylic acid methyl ester, 5 and 1-(5-Bromo-2-hydroxy-benzyl)-3-methyl-1H-pyrazole-4-carboxylic acid methyl ester 6 as a mixture.

LC-MS: m/z 326 M+H$^+$

Step 2

1-[5-Bromo-2-(2-ethyl-butoxy)-benzyl]-5-methyl-1H-pyrazole-4-carboxylic acid methyl ester, 6

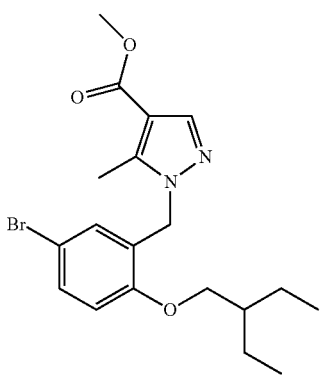 [SMILES: CCC(CC)COc1ccc(Br)cc1Cn1ncc(C(=O)OC)c1C]

The title compound was prepared following the method in Example 1, Step 3.

Step 3

1-[5-Bromo-2-(2-ethyl-butoxy)-benzyl]-5-methyl-1H-pyrazole-4-carboxylic acid, 7

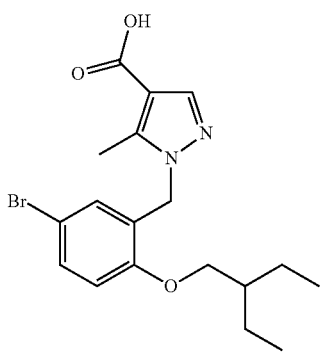

The title compound was prepared following the method in Example 1, Step 4.

$^1$H-NMR (CDCl$_3$, 300 MHz) δ 8.02 (s, 1H, ArH), 7.37 (dd, 1H, ArH), 6.83 (d, 1H, ArH), 6.78 (d, 1H, ArH), 5.21 (s, 2H, ArCH$_2$), 3.90 (d, 2H, CH$_2$), 2.53 (s, 3H, CH$_3$), 1.71 (m, 1H, CH), 1.48 (m, 4H, CH$_2$), 0.96 (t, 6H, CH$_3$).

LC-MS: m/z 396 M+H$^+$

Example 3

1-(5-bromo-2-hydroxy-benzyl)-3-methyl-1H-pyrazole-4-carboxylic acid methyl ester, 9

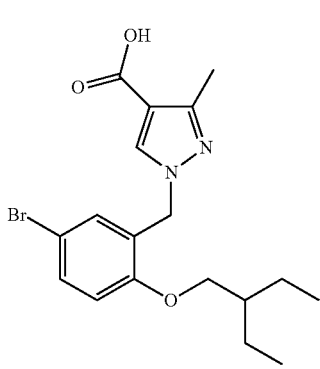

Step 1

1-[5-Bromo-2-(2-ethyl-butoxy)-benzyl]-3-methyl-1H-pyrazole-4-carboxylic acid methyl ester, 8

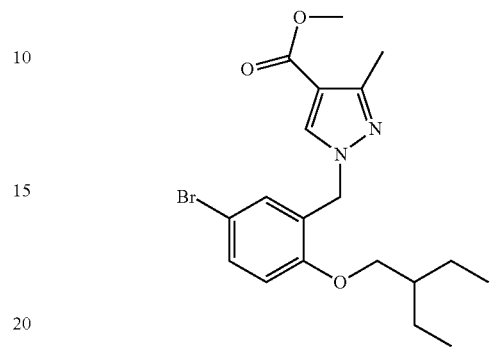

The title compound was prepared using the mixture from Example 2, Step 1 following the method in Example 1, Step 3.

$^1$H-NMR (CDCl$_3$, 300 MHz) δ 7.94 (s, 1H, ArH), 7.35 (dd, 1H, ArH), 6.78 (d, 1H, ArH), 6.77 (s, 1H, ArH), 5.29 (s, 2H, ArCH$_2$), 3.90 (d, 2H, CH$_2$), 3.85 (s, 3H, CH$_3$), 2.51 (s, 3H, CH$_3$), 1.71 (m, 1H, CH), 1.49 (m, 4H, CH$_2$), 0.95 (t, 6H, CH$_3$).

LC-MS: m/z 410 M+H$^+$.

Step 2

1-(5-Bromo-2-hydroxy-benzyl)-3-methyl-1H-pyrazole-4-carboxylic acid methyl ester, 9

The title compound was prepared following the method in Example 1, Step 4.

$^1$H-NMR (CDCl$_3$, 300 MHz) δ 7.84 (s, 1H, ArH), 7.42 (dd, 1H, ArH), 7.25 (d, 1H, ArH), 6.80 (d, 1H, ArH), 5.22 (s, 2H, ArCH$_2$), 3.87 (d, 2H, CH$_2$), 2.50 (s, 3H, CH$_3$), 1.67 (m, 1H, CH), 1.44 (m, 4H, CH$_2$), 0.92 (t, 6H, CH$_3$).

LC-MS: m/z 396 M+H$^+$.

Example 4

1-[5-chloro-2-(2-ethyl-butoxy)-benzyl]-1H-pyrazole-4-carboxylic acid, 14

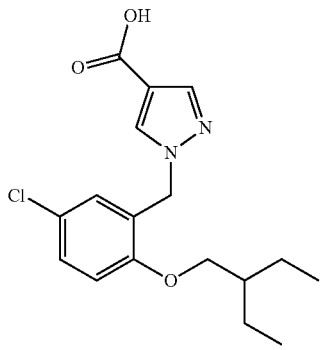 [SMILES: CCC(CC)COc1ccc(Cl)cc1Cn1cc(C(=O)O)cn1]

Step 1

5-Chloro-2-(2-ethyl-butoxy)-benzaldehyde, 10

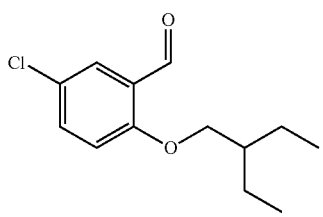 [SMILES: CCC(CC)COc1ccc(Cl)cc1C=O]

To a solution of 5-chloro-2-hydroxybenzaldehyde, 2.1 g (13.4 mmol) DMF (50 mL) under $N_2$ atmosphere at RT was added 3-(chloromethyl)pentane (1.92 g 15.6 mmol), $K_2CO_3$ (4.5 g, 32.6 mmol) and tetrabutylammonium iodide (0.35 g, 0.9 mmol). The resulting mixture was stirred at 120° C. for 5 hours. The mixture was partitioned between water (80 ml) and EtOAc (80 ml). The organic layer was washed with water (80 ml) followed by brine (80 ml), dried over ($Na_2SO_4$), filtered and the volatiles were removed in vacuo. The crude product was purified on silica to yield to yield 2.83 g of 5-Chloro-2-(2-ethyl-butoxy)-benzaldehyde, 10.

1H-NMR, (CDCl$_3$, 300 MHz) δ 10.46 (s, 1H ArCHO,), 7.80 (d, 1H, ArH,), 7.49 (dd, 1H, ArH), 6.97 (d, 1H, ArH), 3.99 (d, 2H, CH$_2$), 1.75 (m, 1H, CH), 1.52 (m, 4H, CH$_2$), 0.97 (t, 6H, CH$_3$).

LC-MS: m/z 241 M+H$^+$.

Step 2

[5-Chloro-2-(2-ethyl-butoxy)-phenyl]methanol, 11

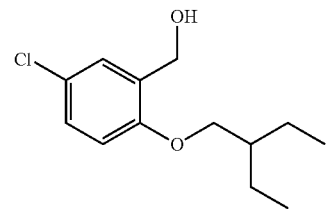 [SMILES: CCC(CC)COc1ccc(Cl)cc1CO]

A solution of 5-Chloro-2-(2-ethyl-butoxy)-benzaldehyde, 10, (2.83 g 11.8 mmol), MeOH (50 mL) was cooled to +5° C. under $N_2$ atmosphere and NaBH$_4$ (0.54 g, 14.2 mmol) was added. The mixture was allowed to warm to RT over 2 hours and the volatiles were removed in vacuo. The reaction mixture was partitioned between water and CH$_2$Cl$_2$. The organic layer was washed with sat. brine, dried (Na$_2$SO$_4$) and evaporated to dryness to give 2.61 g of 5-chloro-2-(2-ethyl-butoxy)-phenyl]-methanol, 11 as a pale yellow oil.

$^1$H-NMR (CDCl$_3$, 300 MHz) δ 7.30 (d, 1H, ArH,), 7.22 (dd, 1H, ArH), 6.82 (d, 1H, ArH), 4.68 (d, 2H, CH$_2$), 3.91 (d, 2H, CH$_2$), 2.22 (t, 1H, CH$_2$OH), 1.71 (m, 1H, CH), 1.50 (m, 4H, CH$_2$), 0.96 (t, 6H, CH$_3$).

LC-MS: m/z 243 M+H$^+$.

Step 3

Methanesulfonic acid 5-chloro-2-(2-ethyl-butoxy)-benzyl ester, 12

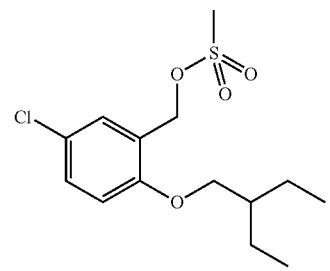 [SMILES: CCC(CC)COc1ccc(Cl)cc1COS(C)(=O)=O]

A solution of [5-Chloro-2-(2-ethyl-butoxy)-phenyl]-methanol, 11, (0.3 g g 1.24 mmol), di-isopropyl-ethyl amine (0.24 mL, 1.36 mmol) and methanesulfonic anhydride (0.24 g 1.36 mmol) in CH$_2$Cl$_2$ (8 mL) was stirred under $N_2$ atmosphere at RT for 2 hours. The reaction mixture was partitioned between water and CH$_2$Cl$_2$. The organic layer was washed with sat. brine, dried (MgSO$_4$) and evaporated to dryness to give mesylate 12, 0.39 g.

¹H-NMR (CDCl₃, 300 MHz) δ 7.38 (d, 1H, ArH,), 7.32 (dd, 1H, ArH), 6.86 (d, ArH), 5.26 (d, 2H, CH₂), 3.90 (d, 2H, CH₂), 3.01 (s, 3H, CH₃), 1.71 (m, 1H, CH), 1.50 (m, 4H, CH₂), 0.95 (t, 6H, CH₃).

Step 4

1-[5-Chloro-2-(2-ethyl-butoxy)-benzyl]-1H-pyrazole-4-carboxylic acid ethyl ester, 13

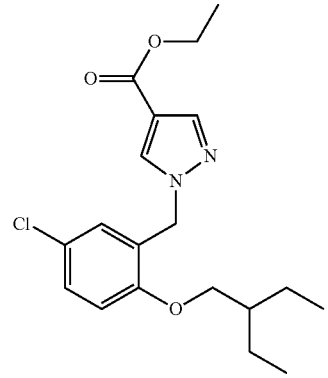 [SMILES: CCOC(=O)c1cnn(Cc2cc(Cl)ccc2OCC(CC)CC)c1]

To a solution of ethyl-4-pyrazole carboxylate, 0.094 g (0.67 mmol) DMF (5 mL) under N₂ atmosphere at RT was added NaH (0.033 g 0.81 mmol, 60% in mineral oils). The resulting mixture was stirred for 30 minutes. A solution of Methanesulfonic acid 5-chloro-2-(2-ethyl-butoxy)-benzyl ester, 12, in DMF (2 mL) was the added and the mixture was stirred for 16 hours. The mixture was poured into water and the volatiles were removed in vacuo. The crude product was purified on silica to yield to yield 0.1 g of 1-[5-Chloro-2-(2-ethyl-butoxy)-benzyl]-1H-pyrazole-4-carboxylic acid ethyl ester, 13.

¹H-NMR (CDCl₃, 300 MHz) δ 7.94 (s, 1H, ArH), 7.87 (s, 1H, ArH), 7.27 (dd, 1H, ArH), 7.08 (d, 1H, ArH), 6.84 (d, 1H, ArH), 5.29 (s, 2H, ArCH₂), 4.30 (q, 2H, CH₃CH₂), 3.88 (d, 2H, CH₂), 1.67 (m, 1H, CH), 1.47 (m, 4H, CH₂), 1.35 (t, 3H, CH₂CH₃), 0.93 (t, 6H, CH₃). LC-MS: m/z 365 M+H⁺.

Step 5

1-[5-Chloro-2-(2-ethyl-butoxy)-benzyl]-1H-pyrazole-4-carboxylic acid, 14

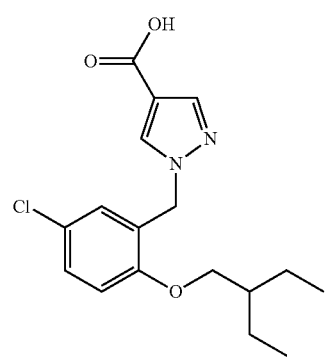 [SMILES: CCC(CC)COc1ccc(Cl)cc1Cn1cc(C(=O)O)cn1]

The title compound was prepared following the method in Example 1, Step 4.

¹H-NMR (CDCl₃, 300 MHz) δ 8.00 (s, 1H, ArH), 7.93 (s, 1H, ArH), 7.29 (dd, 1H, ArH), 7.14 (d, 1H, ArH), 6.85 (d, 1H, ArH), 5.31 (d, 2H, ArCH₂), 3.88 (d, 2H, CH₂), 1.67 (m, 1H, CH), 1.43 (m, 4H, CH₂), 1.35 (t, 3H, CH₂CH₃), 0.92 (t, 6H, CH₃).

LC-MS: m/z 337 M+H⁺.

Example 5

1-[5-chloro-2-(2-ethyl-butoxy)-benzyl]-3,5-dimethyl-1H-pyrazole-4-carboxylic acid, 16

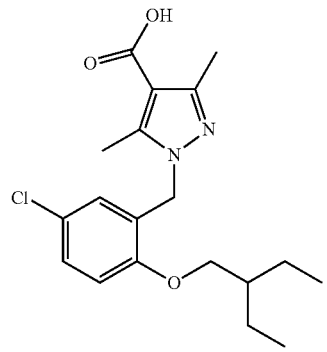 [SMILES: CCC(CC)COc1ccc(Cl)cc1Cn1nc(C)c(C(=O)O)c1C]

Step 1

1-[5-Chloro-2-(2-ethyl-butoxy)-benzyl]-3,5-dimethyl-1H-pyrazole-4-carboxylic acid ethyl ester, 15

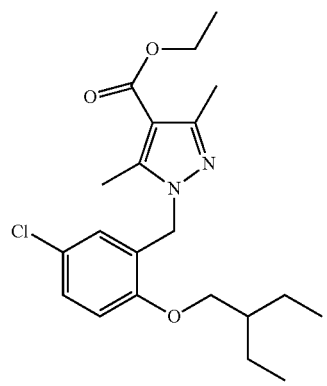 [SMILES: CCOC(=O)c1c(C)nn(Cc2cc(Cl)ccc2OCC(CC)CC)c1C]

The title compound was prepared following the method in Example 4, Step 4.

¹H-NMR (CDCl₃, 300 MHz) δ 7.18 (dd, 1H, ArH), 6.81 (d, 1H, ArH), 6.55 (d, 1H, ArH), 5.23 (d, 2H, ArCH₂), 4.14 (q, 2H, CH₃CH₂), 3.90 (d, 2H, CH₂), 2.47 (s, 3H, CH₃), 2.45 (s,

3H, CH$_3$), 1.71 (m, 1H, CH), 1.50 (m, 4H, CH$_2$), 1.38 (t, 3H, CH$_2$CH$_3$), 0.95 (t, 6H, CH$_3$). LC-MS: m/z 393 M+H$^+$.

Step 2

1-[5-Chloro-2-(2-ethyl-butoxy)-benzyl]-3,5-dimethyl-1H-pyrazole-4-carboxylic acid, 16

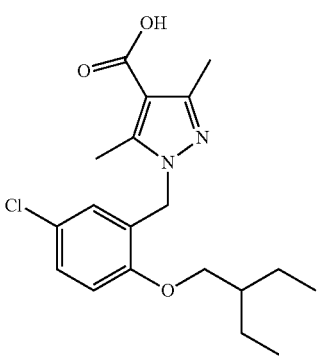 [SMILES: CCC(CC)COc1ccc(Cl)cc1Cn1nc(C)c(C(=O)O)c1C]

The title compound was prepared following the method in Example 1, Step 4.

$^1$H-NMR (CDCl$_3$, 300 MHz) δ 7.20 (dd, 1H, ArH), 6.82 (d, 1H, ArH), 6.62 (d, 1H, ArH), 5.26 (s, 2H, ArCH$_2$), 3.91 (d, 2H, CH$_2$), 2.51 (s, 3H, CH$_3$), 2.50 (s, 3H, CH$_3$), 1.72 (m, 1H, CH), 1.50 (m, 4H, CH$_2$), 1.38 (t, 3H, CH$_2$CH$_3$), 0.96 (t, 6H, CH$_3$).

LC-MS: m/z 365 M+H$^+$.

Example 6

1-[5-chloro-2-(2-ethyl-butoxy)-benzyl]-3-propyl-1H-pyrazole-4-carboxylic acid, 18

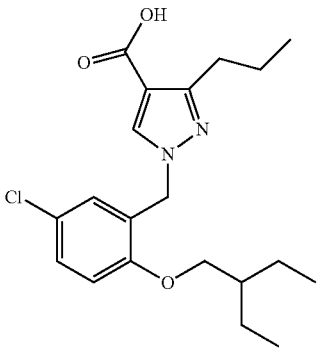 [SMILES: CCCc1nn(Cc2cc(Cl)ccc2OCC(CC)CC)cc1C(=O)O]

Step 1

1-[5-Chloro-2-(2-ethyl-butoxy)-benzyl]-3-propyl-1H-pyrazole-4-carboxylic acid ethyl ester, 17

The title compound and its region-isomer (2:1 mixture) were prepared following the method in Example 4, Step 4. The mixture was in subsequent step.

LC-MS: m/z 407 M+H$^+$.

Step 2

1-[5-Chloro-2-(2-ethyl-butoxy)-benzyl]-3-propyl-1H-pyrazole-4-carboxylic acid, 18

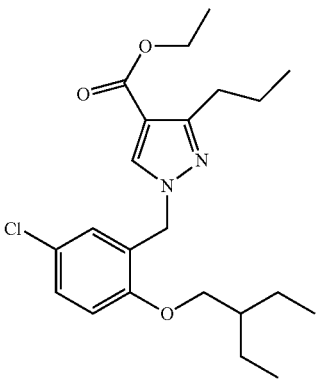 [SMILES: CCCc1nn(Cc2cc(Cl)ccc2OCC(CC)CC)cc1C(=O)OCC]

The title compound was prepared following the method in Example 1, Step 4.

$^1$H-NMR (CDCl$_3$, 300 MHz) δ 8.02 (s, 1H, ArCOOH), 7.22 (dd, 1H, ArH), 7.06 (d, 1H, ArH), 6.83 (d, 1H, ArH), 6.71 (d, 1H, ArH), 5.32 (d, 2H, ArCH$_2$), 3.91 (d, 2H, CH$_2$), 2.93 (t, 2H, ArCH$_2$CH$_2$), 1.83 (m, 1H, CH), 1.56 (m, 2H, CH$_2$CH$_2$), 1.50 (m, 4H, CH$_2$), 0.96 (t, 6H, CH$_3$), 0.95 (t, 3H, CH$_2$CH$_3$).

LC-MS: m/z 379 M+H$^+$.

Example 7

1-[5-chloro-2-(2-ethyl-butoxy)-benzyl]-5-propyl-1H-pyrazole-4-carboxylic acid, 20

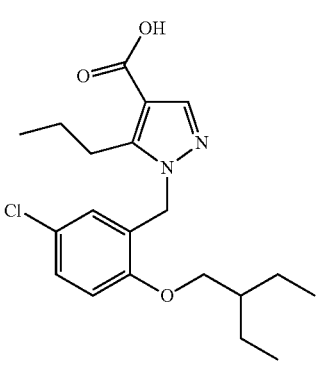 [SMILES: CCCc1c(C(=O)O)cnn1Cc1cc(Cl)ccc1OCC(CC)CC]

27

Step 1

1-[5-Chloro-2-(2-ethyl-butoxy)-benzyl]-5-propyl-1H-pyrazole-4-carboxylic acid ethyl ester, 19

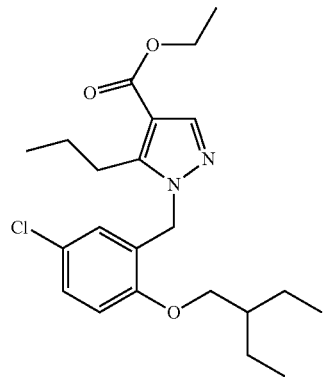 [SMILES: CCCc1c(C(=O)OCC)cnn1Cc1cc(Cl)ccc1OCC(CC)CC]

The title compound and its region-isomer (2:1 mixture) were prepared following the method in Example 4, Step 4. The mixture was used in subsequent step.

LC-MS: m/z 407 M+H$^+$.

Step 2

1-[5-Chloro-2-(2-ethyl-butoxy)-benzyl]-5-propyl-1H-pyrazole-4-carboxylic acid, 20

The title compound was prepared following the method in Example 1, Step 4.

$^1$H-NMR (CDCl$_3$, 300 MHz) δ 7.83 (d, 1H, ArH), 7.27 (dd, 1H, ArH), 7.06 (d, 1H, ArH), 6.84 (d, 1H, ArH), 5.24 (s, 2H, ArCH$_2$), 3.88 (d, 2H, CH$_2$), 2.88 (t, 2H, ArCH$_2$CH$_2$), 1.74 (m, 2H, CH$_2$CH$_2$), 1.66 (m, 1H, CH), 1.43 (m, 4H, CH$_2$), 0.99 (t, 3H, CH$_2$CH$_3$), 0.91 (t, 6H, CH$_3$).

LC-MS: m/z 379 M+H$^+$.

Example 8

1-[2-(2-ethyl-butoxy)-5-trifluoromethyl-benzyl]]-5-methyl-1H-pyrazole-4-carboxylic acid, 25

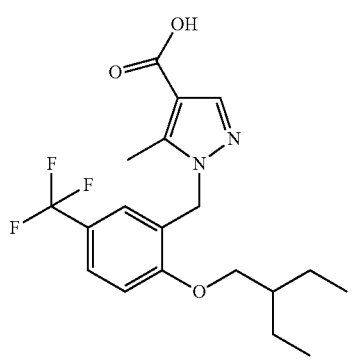 [SMILES: CCC(CC)COc1ccc(C(F)(F)F)cc1Cn1ncc(C(=O)O)c1C]

28

Step 1

2-Bromomethyl-1-methoxy-4-trifluoromethyl-benzene, 21

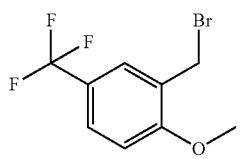

To a solution of 2-methoxy-5-trifluorobenzyl alcohol, 1 g (4.85 mmol) DCM (20 mL) under N$_2$ atmosphere at RT was added PBr$_3$ (5.82 mL, 5.82 mmol, 1M in DCM). The resulting mixture was stirred for 16 hours. The reaction mixture was quenched with saturated NaHCO$_3$ and partitioned between aqueous phase and CH$_2$Cl$_2$. The organic layer was washed with sat. brine, dried (MgSO$_4$) and evaporated to dryness to give 1.1 g of 2-bromomethyl-1-methoxy-4-trifluoromethyl-benzene, 21.

$^1$H-NMR (CDCl$_3$, 300 MHz) δ 7.61 (s, 1H, ArH,), 7.58 (d, 1H, ArH), 6.97 (d, 1H, ArH), 4.56 (d, 2H, CH$_2$), 3.97 (d, 2H, CH$_2$).

LC-MS: m/z 270 M+H$^+$.

Step 2

1-(2-Methoxy-5-trifluoromethyl-benzyl)-5-methyl-1H-pyrazole-4-carboxylic acid ethyl ester, 22

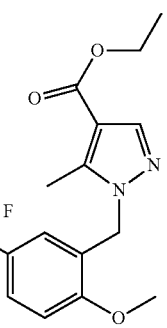

To a solution of ethyl-4-pyrazole carboxylate, 1.1 g (4.09 mmol) in DMF (37 mL) under N$_2$ atmosphere at RT was added NaH (0.22 g, 5.32 mmol, 60% in mineral oils). The resulting mixture was stirred for 30 minutes. A solution of 2-bromomethyl-1-methoxy-4-trifluoromethyl-benzene 21 in DMF (2 mL) (0.69 g, 4.5 mmol) was then added and the mixture was stirred for 16 hours. The mixture was poured into water and the volatiles were removed in vacuo. The crude product was purified on silica to yield 1 g of 1-[5-Chloro-2-(2-ethyl-butoxy)-benzyl]-1H-pyrazole-4-carboxylic acid ethyl ester, 22 as a 3:2 mixture with its regioisomer. The mixture was used in subsequent step.

LC-MS: m/z 343 M+H$^+$.

Step 3

1-(2-Hydroxy-5-trifluoromethyl-benzyl)-5-methyl-1H-pyrazole-4-carboxylic acid ethyl ester, 23

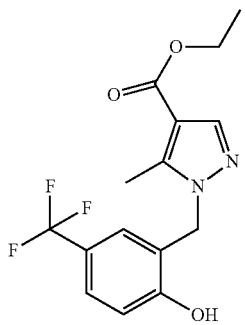 [SMILES: CCOC(=O)c1cnn(Cc2cc(C(F)(F)F)ccc2O)c1C]

To a solution of 1-(2-Methoxy-5-trifluoromethyl-benzyl)-5-methyl-1H-pyrazole-4-carboxylic acid ethyl ester, 22, 0.2 g (0.60 mmol) in dry DCM (25 ml) under $N_2$ atm at 0° C., 4.4 ml of boron tribromide (1M in DCM) was added. The solution was allowed to warm to room temperature. The mixture was stirred for 24 hours, quenched with MeOH and refluxed for 3 hours. Cooled to room temperature, water was added, extracted with EtOAc and wash with brine. After drying over $MgSO_4$ solvents were removed in vacuo and the crude product was purified on silica to yield 0.18 g of 1-(2-Chloro-5-hydroxy-benzyl)-1H-indazole-5-carboxylic acid methyl ester, 23 as a 3:2 mixture with its regio isomer. The mixture was used in subsequent step.

LC-MS: m/z 329 M+H$^+$.

Step 4

1-[2-(2-Ethyl-butoxy)-5-trifluoromethyl-benzyl]-5-methyl-1H-pyrazole-4-carboxylic acid, ethyl ester, 24

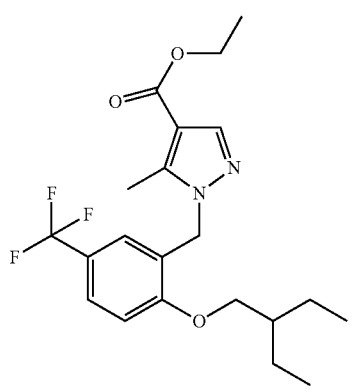 [SMILES: CCOC(=O)c1cnn(Cc2cc(C(F)(F)F)ccc2OCC(CC)CC)c1C]

The title compound was prepared following the method in Example 1, Step 3, as a 3:2 mixture with its regioisomer. The mixture was used in subsequent step.

LC-MS: m/z 413 M+H$^+$.

Step 5

1-[2-(2-Ethyl-butoxy)-5-trifluoromethyl-benzyl]-5-methyl-1H-pyrazole-4-carboxyli acid, 25

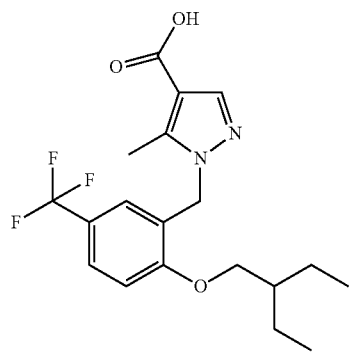 [SMILES: CCC(CC)COc1ccc(C(F)(F)F)cc1Cn1ncc(C(=O)O)c1C]

The title compound was prepared following the method in Example 1, Step 4. The title isomer was separated from the mixture by RP-HPLC.

$^1$H-NMR (CDCl$_3$, 300 MHz) δ 8.01 (s, 1H, ArH), 7.54 (m, 1H, ArH), 7.00 (m, 1H, ArH), 6.98 (m, 1H, ArH), 5.34 (s, 2H, ArCH$_2$), 3.98 (d, 2H, CH$_2$), 2.54 (s, 3H, CH$_3$), 1.74 (m, 1H, CH), 1.49 (m, 4H, CH$_2$), 0.96 (t, 6H, CH$_3$).

LC-MS: m/z 385 M+H$^+$

Example 9

1-[2-(2-ethyl-butoxy)-5-trifluoromethyl-benzyl]-3-methyl-1H-pyrazole-4-carboxylic acid, 26

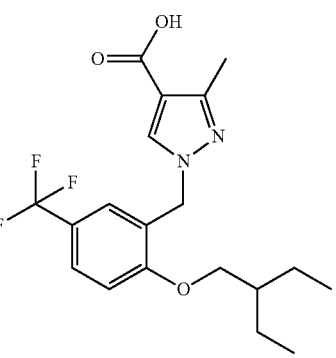

The title compound was prepared from the product of Example 8 step 4 following the method in Example 1, Step 4. The title isomer was separated from the mixture by RP-HPLC.

$^1$H-NMR (CDCl$_3$, 300 MHz) δ 7.84 (s, 1H, ArH), 7.60 (m, 1H, ArH), 7.41 (m, 1H, ArH), 6.99 (d, 1H, ArH), 5.28 (s, 2H, ArCH$_2$), 3.95 (d, 2H, CH$_2$), 2.47 (s, 3H, CH$_3$), 1.69 (m, 1H, CH), 1.45 (m, 4H, CH$_2$), 0.92 (t, 6H, CH$_3$).

LC-MS: m/z 385 M+H$^+$

Example 10

1-[5-chloro-2-(2-ethyl-butoxy)-benzyl]-5-methyl-1H-pyrazole-4-carboxylic acid, 28

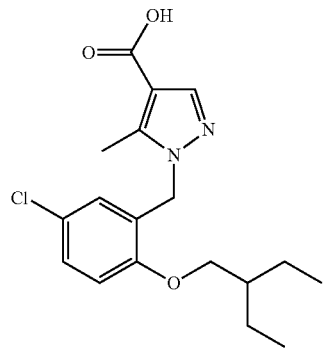 [SMILES: CCC(CC)COc1ccc(Cl)cc1Cn1ncc(C(=O)O)c1C]

Step 1

1-[5-Chloro-2-(2-ethyl-butoxy)-benzyl]-5-methyl-1H-pyrazole-4-carboxylic acid ethyl ester, 27

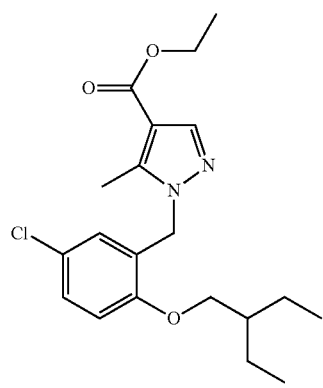 [SMILES: CCOC(=O)c1cnn(Cc2cc(Cl)ccc2OCC(CC)CC)c1C]

The title compound was prepared following the method in Example 4, Step 4.

$^1$H-NMR (CDCl$_3$, 300 MHz) δ 8.01 (s, 1H, ArH), 7.20 (dd, 1H, ArH), 6.82 (d, 1H, ArH), 6.61 (d, 1H, ArH), 5.29 (s, 2H, ArCH$_2$), 4.32 (q, 2H, CH$_3$CH$_2$), 3.90 (d, 2H, CH$_2$), 2.50 (s, 3H, CH$_3$), 1.71 (m, 1H, CH), 1.49 (m, 4H, CH$_2$), 1.38 (t, 2H, CH$_3$CH$_2$), 0.96 (t, 6H, CH$_3$).

LC-MS: m/z 379 M+H$^+$

Step 2

1-[5-Chloro-2-(2-ethyl-butoxy)-benzyl]-5-methyl-1H-pyrazole-4-carboxylic acid, 28

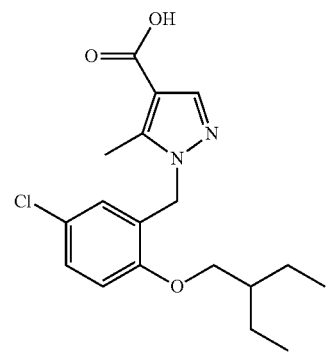 [SMILES: CCC(CC)COc1ccc(Cl)cc1Cn1ncc(C(=O)O)c1C]

The title compound was prepared following the method in Example 1, Step 4.

$^1$H-NMR (CDCl$_3$, 300 MHz) δ 8.03 (s, 1H, ArH), 7.23 (dd, 1H, ArH), 6.83 (d, 1H, ArH), 6.69 (d, 1H, ArH), 5.31 (s, 2H, ArCH$_2$), 3.92 (d, 2H, CH$_2$), 2.53 (s, 3H, CH$_3$), 1.72 (m, 1H, CH), 1.49 (m, 4H, CH$_2$), 0.96 (t, 6H, CH$_3$).

LC-MS: m/z 351 M+H$^+$

Example 11

1-(5-chloro-2-isobutoxy-benzyl)-5-methyl-1-pyrazole-4-carboxylic acid, 29

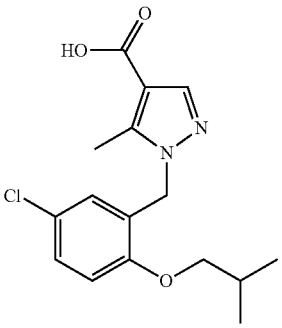 [SMILES: Cc1c(C(=O)O)cnn1Cc1cc(Cl)ccc1OCC(C)C]

The title compound was prepared following the methods described for Example 8 and using the appropriate starting materials and reagents $^1$H-NMR (CDCl$_3$, 300 MHz) δ 8.05 (s, 1H, ArH), 7.20 (dd, 1H, ArH), 6.80 (d, 1H, ArH), 6.70 (d, 1H, ArH), 5.31 (s, 2H, ArCH$_2$), 3.78 (d, 2H, CH$_2$), 2.55 (s, 3H, CH$_3$), 2.15 (m, 1H, CH), 1.03 (d, 6H, CH$_3$).

LC-MS: m/z 323 M+H$^+$

Example 12

1-(5-chloro-2-cyclopentylmethoxy-benzyl)-5-methyl-1H-pyrazole-4-carboxylic acid, 30

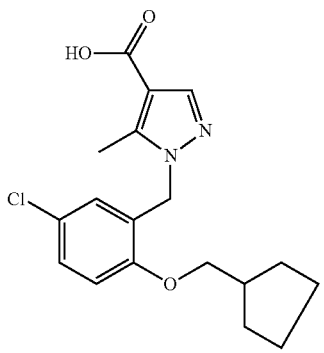 [SMILES: Cc1c(C(=O)O)cnn1Cc1cc(Cl)ccc1OCC1CCCC1]

The title compound was prepared following the methods described for Example 8 and using the appropriate starting materials and reagents $^1$H-NMR (DMSO, 300 MHz) δ 7.55 (s, 1H, ArH), 7.33 (dd, 1H, ArH), 7.05 (d, 1H, ArH), 6.80 (m, 1H, ArH), 5.25 (s, 2H, ArCH$_2$), 3.90 (d, 2H, CH$_2$), 2.55 (s, 3H, CH$_3$), 2.27 (m, 1H, CH), 1.75 (m, 2H, CH$_2$CH$_2$), 1.6 (m, 4H, —CH$_2$—CH$_2$—), 1.30 (m, 2H, —CH$_2$—CH$_2$—).

LC-MS: m/z 349 M+H$^+$

Example 13

1-(5-bromo-2-isobutoxy-benzyl)-5-methyl-1H-pyrazole-4-carboxylic acid, 31

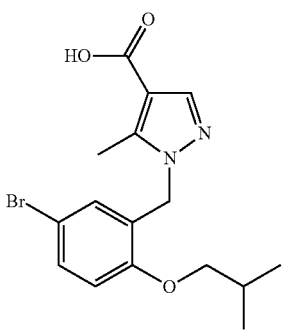

The title compound was prepared following the methods described for Example 8 and using the appropriate starting materials and reagents.

$^1$H-NMR (CDCl$_3$, 300 MHz) δ 8.03 (s, 1H, ArH), 7.35 (dd, 1H, ArH), 6.87 (s, 1H, ArH), 6.75 (d, 1H, ArH), 5.31 (s, 2H, ArCH$_2$), 3.75 (d, 2H, CH$_2$), 2.55 (s, 3H, CH$_3$), 2.15 (m, 1H, CH), 1.03 (d, 6H, CH$_3$).

LC-MS: m/z 369 M+H$^+$

Example 14

1-[5-bromo-2-(2,2-dimethyl-propoxy)-benzyl]-5-methyl-1H-pyrazole-4-carboxylic acid, 32

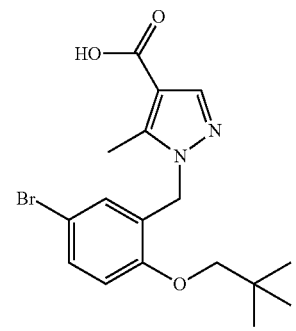 [SMILES: Cc1c(C(=O)O)cnn1Cc1cc(Br)ccc1OCC(C)(C)C]

The title compound was prepared following the methods described for Example 8 and using the appropriate starting materials and reagents.

$^1$H-NMR (CDCl$_3$, 300 MHz) δ 8.05 (s, 1H, ArH), 7.35 (dd, 1H, ArH), 6.80 (s, 1H, ArH), 6.75 (d, 1H, ArH), 5.40 (s, 2H, ArCH$_2$), 3.65 (s, 2H, CH$_2$), 2.52 (s, 3H, CH$_3$), 1.05 (s, 9H, CH$_3$).

LC-MS: m/z 383 M+H$^+$

Example 15

1-[2-(2-ethyl-butoxy)-5-trifluoromethoxy-benzyl]-5-methyl-1H-pyrazole-4-carboxylic acid, 33

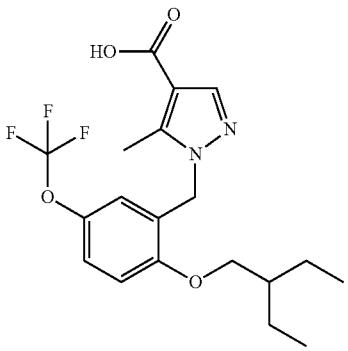 [SMILES: CCC(CC)COc1ccc(OC(F)(F)F)cc1Cn1ncc(C(=O)O)c1C]

The title compound was prepared following the methods described for Example 8 and using the appropriate starting materials and reagents.

$^1$H-NMR (CDCl$_3$, 300 MHz) δ 8.05 (s, 1H, ArH), 7.15 (dd, 1H, ArH), 6.90 (d, 1H, ArH), 6.60 (d, 1H, ArH), 5.32 (s, 2H, ArCH$_2$), 3.95 (d, 2H, CH$_2$), 2.55 (s, 3H, CH$_3$), 1.75 (m, 1H, CH), 1.52 (q, 4H, CH$_2$), 1.00 (t, 6H, CH$_3$).

LC-MS: m/z 401 M+H$^+$

Example 16

5-amino-1-[5-bromo-2-(2-ethyl-butoxy)-benzyl]-1H-pyrazole-4-carboxylic acid, 36

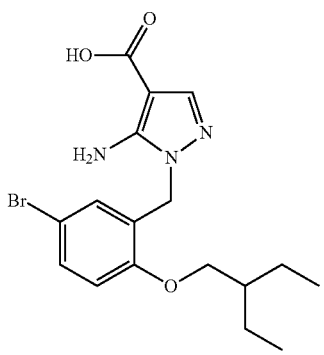 [SMILES: CCC(CC)COc1ccc(Br)cc1Cn1ncc(C(=O)O)c1N]

Step 1

5-Amino-1-(5-bromo-2-hydroxy-benzyl)-1H-pyrazole-4-carboxylic acid, 34

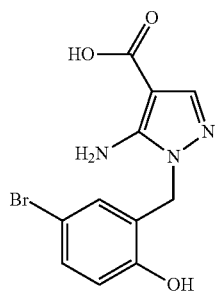 [SMILES: Nc1c(C(=O)O)cnn1Cc1cc(Br)ccc1O]

A suspension of N'-(5-bromo-2-hydroxy-benzyl)-hydrazinecarboxylic acid tert-butyl ester 1 (1 g, 3.1 mmol) in a mixture of CH$_2$Cl$_2$ (8 mL) and TFA (8 mL) was stirred at RT for 2 hours. The volatiles were removed in vacuo. The residue was dissolved in abs. EtOH (15 mL) and ethyl-2-cyano-3-ethoxyacrylate (0.55 g, 3.3 mmol) was added at RT. The resulting mixture was refluxed for 6 h, let cool down and stirred at RT for 16 h.

The white solid residue obtained was suspended with EtOAc (10 ml) volatiles were removed in vacuo. The remaining oily residue was triturated with ether, collected and washed once with ether to give 0.3 g of the title compound as a white solid.

$^1$H-NMR (DMSO-D$_6$, 300 MHz) δ 10.17 (s, 1H, ArOH), 7.53 (s, 1H, ArH), 7.27 (dd, 1H, ArH), 6.80 (d, 1H, ArH), 6.71 (d, 1H, ArH), 6.33 (s, 2H, ArNH$_2$), 5.05 (s, 2H, ArCH$_2$), 4.17 (q, 2H, —CH$_2$CH$_3$), 1.25 (t, 3H, —CH$_2$CH$_3$).

LC-MS: m/z 340,342 M+H$^+$

Step 2

5-amino-1-[5-bromo-2-(2-ethyl-butoxy)-benzyl]-1h-pyrazole-4-carboxylic acid ethyl ester, 35

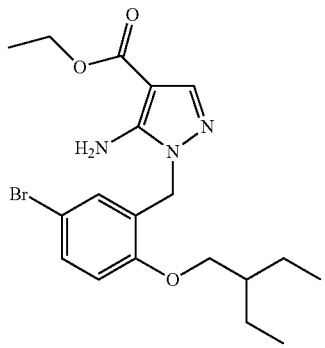 [SMILES: CCOC(=O)c1cnn(Cc2cc(Br)ccc2OCC(CC)CC)c1N]

The title compound was prepared following the method in Example 1, Step 3.

$^1$H-NMR (CDCl$_3$, 300 MHz) δ 7.67 (s, 1H, ArH), 7.39 (dd, 1H, ArH), 7.26 (d, 1H, ArH), 6.82 (d, 1H, ArH), 5.23 (s, 2H, ArNH$_2$), 5.10 (s, 2H, ArCH$_2$), 4.28 (q, 2H, —CH$_2$CH$_3$), 3.95 (dd, 2H, CH$_2$), 1.73 (m, 1H, CH), 1.51 (m, 4H, CH$_2$), 1.35 (t, 3H, —CH$_2$CH$_3$), 0.97 (t, 6H, CH$_3$).

LC-MS: m/z 424,426 M+H$^+$

Step 3

5-amino-1-[5-bromo-2-(2-ethyl-butoxy)-benzyl]-1h-pyrazole-4-carboxylic acid, 36

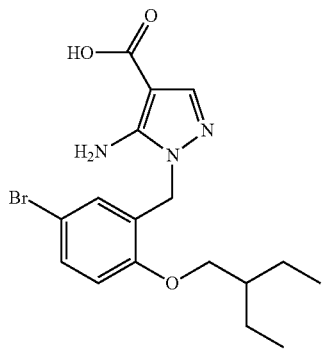 [SMILES: CCC(CC)COc1ccc(Br)cc1Cn1ncc(C(=O)O)c1N]

The title compound was prepared following the method in Example 1, Step 4

$^1$H-NMR (CDCl$_3$, 300 MHz) δ 7.72 (s, 1H, ArH), 7.40 (dd, 1H, ArH), 7.32 (d, 1H, ArH), 6.83 (d, 1H, ArH), 5.32 (s, 2H, ArNH$_2$), 5.11 (s, 2H, ArCH$_2$), 3.95 (dd, 2H, CH$_2$), 1.74 (m, 1H, CH), 1.52 (m, 4H, CH$_2$), 1.35 (t, 3H, —CH$_2$CH$_3$), 0.97 (t, 6H, CH$_3$).

LC-MS: m/z 396,398 M+H$^+$

The above compounds were tested for PG antagonist activity as follows using human recombinant prostanoid receptor (DP$_1$, EP$_{1-4}$, FP, IP and TP) stable cell lines:

In order to measure the response of G$_s$ and G$_i$ coupled prostanoid receptors as a Ca$^{2+}$ signal, chimeric G protein cDNAs were used. Stable cell lines over-expressing human prostanoid DP$_1$, EP$_{1-4}$, FP, IP, and TP receptors were established as follows:

Briefly, human prostanoid $DP_1$, $EP_2$, and $EP_4$ receptor cDNAs were co-transfected with chimeric $G_{qs}$ cDNA containing a haemagglutanin (HA) epitope; human prostanoid $EP_3$ receptors were co-transfected with chimeric $G_{qi}$-HA; human $EP_1$, FP, IP, and TP receptor cDNAs were expressed with no exogenous G-proteins. $G_{qs}$ and $G_{qi}$ chimeric cDNAs (Molecular Devices, Sunnyvale, Calif., U.S.A.), as well as cDNAs of prostanoid receptors, were cloned into a $pCEP_4$ vector with a hygromycin B selection marker. Transfection into HEK-293 EBNA (Epstein-Barr virus nuclear antigen) cells was achieved by the FuGENE 6 transfection Reagent (Roche Applied Science, Indianapolis, Ind., USA). Stable transfectants were selected according to hygromycin resistance. Because $G_{qs}$ and $G_{qi}$ contained an HA epitope, G-protein expression was detected by Western blotting analysis using anti-mouse HA monoclonal antibody and horseradish peroxidase (HRP)-conjugated secondary antibody, while functional expression of prostanoid receptors was detected by FLIPR screening (Matias et al., 2004). These stable cell lines were validated using previously published antagonists at 10 µM against serial dilutions of standard agonists by FLIPR functional assays for $Ca^{2-}$ Signaling (as described below).

$Ca^{2+}$ signaling studies were performed using a FLIPR TETRA system (Molecular Devices, Sunnyvale, Calif., USA) in the 384-format. This is a high-throughput instrument for cell-based assays to monitor $Ca^{2+}$ signaling associated with GPCRs and ion channels. Cells were seeded at a density of $5 \times 10^4$ cells/well in BioCoat poly-D-lysine coated, black wall, clear bottom 384-well plates (BD Biosciences, Franklin lakes, N.J., USA) and allowed to attach overnight in an incubator at 37° C. The cells were then washed twice with HBSS-HEPES buffer (Hanks' balanced salt solution without bicarbonate and phenol red, 20 mM HEPES, pH 7.4) using an ELx405 Select CW Microplate Washer (BioTek, Winooski, Vt., USA). After 60 min of dye-loading in the dark using the $Ca^{2+}$-sensitive dye Fluo-4AM (Invitrogen, Carlsbad, Calif., USA), at a final concentration of $2 \times 10^{-6}M$, the plates were washed 4 times with HBSS-HEPES buffer to remove excess dye and leaving 50 µl of buffer in each well. The plates were then placed in the FLIPR TETRA instrument and allowed to equilibrate at 37° C. AGN-211377 was added in a 25 µl volume to each well to give final concentrations of 0.1 µM, 0.3 µM, 1 µM, 3 µM, 10 µM, and 30 µM; or 0.067 µM, 0.1 µM, 0.2 µM, 0.3 µM, 0.67 µM, and 1 µM for cells over-expressing TP receptors. After 4.5 minutes, a 7-point serial dilution of the standard agonist for the corresponding receptor, in a 25 µl volume was injected at the final concentrations from $10^{-11}M$ to $10^{-5}M$ in 10-fold serial dilution increments for cells expressing human recombinant $DP_1$, $EP_1$, $EP_2$, $EP_3$, $EP_4$, FP, and IP receptors. The dose range for the standard agonist for human recombinant TP receptors was from $10^{-12}M$ to $10^{-6}M$. HBSS-HEPES buffer was used as the negative control for the standard agonists. Cells were excited with LED (light emitting diode) excitation at 470-495 nm and emission was measured through an emission filter at 515-575 nm. Assay plates were read for 3.5 minutes using the FLIPR$^{TETRA}$. The peak increase in fluorescence intensity was recorded for each well. On each plate, negative controls, dose response of positive controls, and co-treatments of antagonist-agonist for each dose were in triplicates. Standard agonists were as follows: DP=BW 245C, $EP_1$-$EP_4$=$PGE_2$, FP=17-phenyl-$PGF_{2\alpha}$, IP=Cicaprost, and TP=U-46619. The peak fluorescence change in each well containing drug was expressed relative to vehicle controls with the standard agonist at $10^{-6}M$ (the positive control). To obtain concentration-response curves, compounds were tested in triplicate in each plate over the desired concentration range.

$Ca^{2+}$ Signal Studies on Human Recombinant Prostanoid Receptor $DP_2$

FLIPR functional assays were conducted at Millipore to monitor the activity anti-asthmatic against human $DP_2$ receptors stably expressed in the Chem-5 proprietary host cell line generated by Millipore. Prior to standard agonist addition, the compounds were spotted at 10 µM along with vehicle control (1% Ethanol in HBSS-HEPES buffer) across the assay wells. The assay plate was incubated at room temperature for 10 minutes in the dark. Then an 8-point serial dilution dose response from $10^{-12}M$ to $10^{-5}M$ of the standard agonist $PGD_2$ was performed. Assay plates were read for 90 seconds using the FLIPR$^{TETRA}$. The fluorescence measurements were collected to calculate $IC_{50}$ values. The assays were done at least 3 times to give n=3.

Data Processing

All plates were subjected to appropriate baseline corrections. Maximum fluorescence values were exported. The raw data of n=1 was first processed by Activity Base using non-linear regression curve fit to calculate the percentage activity of each data point relative to the positive control (=$10^{-6}M$ of the standard agonist). Then n=3 of this data were exported to GraphPad Prism 4 to calculate the average $EC_{50}$ of the standard agonist, and the $IC_{50}$ (the concentration of the antagonist required to inhibit half the standard agonist activity) were calculated using nonlinear regression curve fit, with constraints of bottom constant equal to 0 and top constant equal to 100. Calculation of Kb=[Antagonist Concentration]/($IC_{50}$/$EC_{50}$−1). When no antagonism was detected or when Kb≥10,000 nM, the antagonist is defined as not active (NA).

The results of the above testing are reported in TABLE 1, below.

TABLE 1

| Example | FP | DP | EP1 | EP2 | EP3 | EP4 | IP | TP |
|---|---|---|---|---|---|---|---|---|
| 1 | 2700 | 400 | 170 | NA | NA | 100 | 4800 | 3 |
| 2 | 80 | 600 | 33 | NA | 6100 | 380 | 2400 | 12 |
| 3 | 400 | 1100 | 30 | NA | NA | 1300 | 1400 | 30 |
| 4 | 2000 | 1400 | 140 | NA | NA | 4800 | 3100 | 100 |
| 5 | 700 | 350 | 20 | NA | NA | 860 | 600 | 18 |
| 6 | NA | 5600 | 1500 | 8600 | NA | 4900 | NA | 500 |
| 7 | NA | NA | 640 | NA | NA | 3300 | 1800 | 150 |
| 8 | 200 | 1400 | 40 | NA | NA | 1600 | NA | 45 |
| 9 | 7200 | 3900 | 440 | NA | NA | NA | NA | 440 |
| 10 | 190 | 940 | 50 | NA | 3900 | 500 | 1300 | 6 |
| 11 | 500 | 4550 | 30 | NA | NA | 3300 | 8300 | 80 |
| 12 | 110 | 2500 | 30 | NA | NA | 600 | 2650 | 40 |
| 13 | 70 | 3500 | 30 | NA | NA | 2100 | 7700 | 20 |
| 14 | 90 | 3400 | 30 | NA | NA | 1300 | NA | 20 |
| 15 | 140 | 780 | 45 | NA | NA | 1500 | 10000 | 8 |
| 16 | 200 | 1600 | 60 | NA | NA | 300 | 5100 | 50 |

As shown in TABLE 1, the preferred compounds of this invention are pan antagonists having activity at the FP, DP, $EP_1$, $EP_4$ and TP receptors, but are inactive at the IP, $EP_2$ and $EP_3$ receptors. Thus, these compounds have a biological selectivity profile making them useful in treating diseases and conditions which are mediated by the $EP_2$ and/or $EP_3$ receptors, without the side effects mediated by the FP, DP, $EP_1$, $EP_4$ and TP receptors.

The 4-carboxylic pyrazoles included in the present invention, were compared to 3-carboxylic acids see TABLE 2, below.

TABLE 2

| Example | FP | DP | EP1 | EP2 | EP3 | EP4 | IP | TP |
|---|---|---|---|---|---|---|---|---|
| 17 | 300 | 2300 | 20 | NA | NA | NA | NA | 30 |
| 18 | 1100 | 500 | 60 | NA | NA | 5000 | NA | <1 |
| 19 | 400 | 2400 | 20 | NA | NA | NA | NA | 7 |
| 20 | 230 | 85 | <1 | NA | NA | 4200 | NA | <1 |
| 21 | 70 | 1300 | 10 | NA | 9100 | NA | NA | 1 |

As shown in TABLE 2, the 3-carboxylic acid compounds are active at FP, EP1 and TP receptors but do not have significant activity at the EP4 receptor. In contrast the 4-carboxylic acids of the present invention are active at the FP, EP1, TP and EP4 receptors.

As a result, the 4-carboxylic acid compounds will exhibit more pronounced therapeutic benefit through blockade of the EP4 receptor whilst allowing EP2, EP3 and IP these receptors to maintain their inherent anti-inflammatory and anti-proliferative functions in response to endogenously present prostanoids.

Thus, the compounds of this invention compound may be administered to treat DP1, FP, EP1, TP and/or EP4 receptor mediated diseases or conditions.

For example, said condition or disease may be related to inflammation, or said DP1, FP, EP1, TP and/or EP4 receptor mediated condition or disease may be selected from the group consisting of allergic conditions, asthma, allergic asthma, allergic rhinitis, uveitis and related disorders, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, gangrene, glaucoma, hyperpyrexia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, rheumatoid arthritis, pain, perennial rhinitis, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders.

Said compound may be administered as a surgical adjunct in ophthalmology for cataract removal and artificial lens insertion, ocular implant procedures, photorefractive radial keratotomy and other ophthalmogical laser procedures or as a surgical adjunct in a procedure involving skin incisions, relief of pain and inflammation and scar formation/keloids post-surgery, for treating sports injuries and general aches and pains in muscles and joints.

Preferably, said $DP_1$, FP, $EP_1$, TP, and/or $EP_4$ receptor mediated condition or disease is an $EP_1$ and/or $EP_4$ receptor mediated condition or disease.

Preferably, said $DP_1$, FP, $EP_1$, TP and/or $EP_4$ receptor mediated condition or disease is an allergic condition, e.g. an dermatological allergy, or an ocular allergy, or a respiratory allergy, e.g. nasal congestion, rhinitis, and asthma.

Said condition or disease may be related to pain.

Said condition or disease may be selected from the group consisting of arthritis, migraine, and headache.

Said condition or disease may be associated with the gastrointestinal tract, wherein said condition or disease may be peptic ulcer, heartburn, reflux esophagitis, erosive esophagitis, non-ulcer dyspepsia, infection by *Helicobacter pylori*, alrynitis, and irritable bowel syndrome.

Said condition or disease may be selected from the group consisting of hyperalgesia and allodynia, or said condition or disease may be related to mucus secretion, wherein said mucus secretion is gastrointestinal, or occurs in the nose, sinuses, throat, or lungs.

Said condition or disease is related to abdominal cramping, e.g. said condition or disease may be irritable bowel syndrome.

Said condition or disease may be a bleeding disorder, or a sleep disorder, or mastocytosis.

Said condition or disease may be associated with elevated body temperature, or ocular hypertension and glaucoma, or ocular hypotension.

Said condition may relate to surgical procedures to treat pain, inflammation and other unwanted sequalae wherein said surgical procedure includes incision, laser surgery or implantation. The present invention also relates to a method of treating inflammation resulting from inflammatory diseases characterized by monocytic infiltration caused by the secretion of cytokines and/or chemokines by administration, to a patient in need of said treatment, of a pharmaceutical composition comprising a compound of the present invention.

The current finding that the compounds of this invention are effective in attenuating the production of TNF family cytokines (TNFα), and the classical interleukin-1 (IL-1) family cytokines is especially important. These cytokines exert a broad spectrum of biological and pathological effects. They play key roles in inflammation and RA pathogenesis by stimulating the release of multiple proinflammatory cytokines, including themselves, through the NFκB signaling pathway. Although alleviating the symptoms of RA in 50-65% of patients, a TNFα antibody is very expensive to use compared to chemically synthesized small molecules, inconvenient to administer usually requiring injections, and has been linked to tuberculosis, lymphoma, and other adverse effects. Unlike a TNFα antibody that totally eliminates all circulating TNFα in the system; the compounds of this invention only attenuate the production of TNFα by inhibiting proinflammatory PG receptors. Therefore the adverse effects associated with a TNFα antibody in elevating infectious and cancerous tendency is less likely.

Proinflammatory elements TNF, RANTES, and MCP-1 are involved in the cascade of events in the early and late stages of atherosclerosis. Plasma MCP-1 levels have been linked to cardiovascular disease risk factors in clinical studies. Platelet activation leads to the release of MIP-1α, RANTES, and IL-8, which attract leukocytes and further activate other platelets. These evidences provide a direct linkage between homeostasis, infection, and inflammation and the development of atherosclerosis. The compounds of this invention are able to target multiple biomarkers of inflammation, thrombosis, and atherothrombosis simultaneously, which may confer pharmaceutical potential on the compounds of this invention in treating atherosclerosis and atherothrombosis. As a result, the compounds of this invention are unlikely to be associated with cardiovascular liability as in the case of the COXIBs, conversely it may even have a beneficial effect on cardiovascular function.

In summary, because of their ability to suppress the synthesis of some key proinflammatory cytokines/chemokines IL-8, MCP-1, MDC, RANTES, and TNFα, the compounds of the present invention are not only at least as effective as COXIBs and NSAIDs in RA treatment, but also are a safer therapy in RA treatment. They are also a potential therapy for cardiovascular diseases.

The compounds of this invention treat or prevent inflammation at least in part by the decreasing the amount of the secretion of certain cytokines and/or chemokines that result from the exposure of the patient to a stimulant.

In particular, the secretion of VEGF, MIP-1β, IL-8, MCP-1, MDC, and RANTES is reduced in those instances where said secretions are triggered by lipopolysaccharides (LPS) and or TNFα.

Interleukin-8 (IL-8): functions as a potent chemo attractants and activator of neutrophils, IL-8 is produced in response to stimulation with either IL-1 or TNFα. IL-8 not only accounts for a significant proportion of the chemotactic activity for neutrophils in rheumatoid arthritis (RA) synovial fluids, but also is a potent angiogenic factor in the RA synovium.

Monocyte chemo attractant protein-1 (MCP-1, or CCL-2): is not only believed to play a role in inflammatory diseases characterized by monocytic infiltration, such as RA rheumatoid arthritis, psoriasis, and atherosclerosis, but is also implicated in other diseases, such as atopic dermatitis, renal disease, pleurisy, allergy and asthma, colitis, endometriosis, polymyositis and dermatomyositis, uveitis, restenosis, brain inflammation and obesity. MCP-1 also controls leukocyte trafficking in vascular cells involved in diabetes and diabetes-induced atherosclerosis. MCP-1 antibodies are potential therapeutic agents for treating MCP-1/CCR2-mediated multiple inflammatory diseases.

Tumor necrosis factor α (TNFα): mainly secreted by macrophages and recognized for its importance in activating the cytokine cascade. TNFα stimulates the production of proinflammatory cytokines/chemokines, collagenases, metalloproteinases, and other inflammatory mediators; activates endothelial cells and neutrophils; promotes T- and B-cell growth, as well as stimulating bone resorption. The TNFα antibody infliximab not only decreases the production of local and systemic proinflammatory cytokines/chemokines, but also reduces serum MMP-3 production, nitric oxide synthase activity, VEGF release, and angiogenesis in inflamed joints.

Macrophage-derived chemokine (MDC) induces chemotaxis for monocyte-derived dendritic cells, activated T cells and natural killer (NK) cells (Ho et al., 2003). Highly expressed by the three major cell types involved in allergic inflammation: eosinophils, basophils, and Th2 lymphocytes (Garcia et al., 2005), as well as highly expressed in atopic dermatitis (Pivarcsi et al., 2005), MDC plays a role in inflammatory diseases such as allergic asthma and atopic dermatitis (Ho et al., 2003). Significantly enhanced in keratinocytes of patients with atopic dermatitis, MDC could be a candidate therapeutic target for inflammatory skin disease such as atopic dermatitis (Qi et al., 2009). MDC is also implicated in disease activity of RA. After combination treatment with the disease-modifying anti-rheumatic drugs leflunomide and methotrexate in RA patients, plasma MCP-1 and MDC concentrations were significantly lower, and so was the recruitment of inflammatory cells into the sites of inflammation (Ho et al., 2003). Moreover, MDC also amplify platelet activation and has been associated with the pathogenesis of atherosclerotic disease including thrombosis (Gleissner et al., 2008).

Regulated on Activation, Normal T Cell Expressed and Secreted (RANTES) is a chemo attractant for blood monocytes, memory T-helper cells and eosinophils, and plays an active role in recruiting leukocytes into inflammatory sites. It also stimulates the release of histamine from basophils, activates eosinophils and causes hypodense eosinophils, which is associated with diseases such as asthma and allergic rhinitis. RANTES receptor CCR5 is also expressed on cells involved in atherosclerosis (e.g. monocytes/macrophages, T lymphocytes, or Th1-type cells), and is specialized in mediating RANTES-triggered atherosclerotic plaque formation (Zernecke et al., 2008). Like MCP-1, stimulation with RANTES enhances production of IL-6 and IL-8 in RA fibroblast-like synovial cells; elevated MMP-3 production by chondrocytes, and inhibited proteoglycan synthesis and enhanced proteoglycan release from the chondrocytes (Iwamoto et al., 2008). Both MCP-1 and RANTES were found to play an important role in allergic lung inflammation, lung leukocyte infiltration, bronchial hyper-responsiveness, and the recruitment of eosinophils in the pathogenesis of asthma (Conti et al., 2001). Similar to MCP-1, RANTES also enhances the inflammatory response within the nervous system, which plays an apparent role in the pathogenesis of multiple sclerosis (Conti et al., 2001). Inhibitors for RANTES may provide clinical benefits in treating inflammation, CNS disorders, parasitic disease, cancer, autoimmune and heart diseases (Castellani et al., 2007).

While the use of the compounds of this invention are shown to decrease the secretion of the above cytokines in FIGS. 2 through 9, it is believed that the compounds of this invention are effective to decrease the secretion of ENA-7, PAI-1, CD-10, G-CSF, GM-CSF, IL-1ά and IL-18, as well.

The compounds of this invention may be also tested for efficacy in treating uveitis as described below.

Arachidonate Induced Uveitis

The rational for this protocol is to use arachidonate to directly produce ocular anterior segment uveitis, as opposed to using lipopolysaccharide (LPS) to indirectly release arachidonic acid.

Induction of Uveitis:

Conscious male or female Dutch-belted pigmented rabbits weighing 2.5-3 kg were used for all in vivo slit lamp studies. Four animals were employed per test group. The right eye of each animal receiving 35 μl of topically administered test and the contralateral left eye of each animal receiving 35 μl of topically administered vehicle (t=0 minutes), followed 30 minutes later by treatment with 35 μl of 0.5% sodium arachidonate onto the surface of both eyes (t=30 minutes). Both eyes were examined by slit lamp 60 minutes following sodium arachidonate challenge (t=90 minutes) at 16× magnification under both white light and blue light illumination at an approximate angle of 45° through 1 mm and 5 mm slit widths.

Measurement of Anterior Chamber Leukocyte Infiltration:

Anterior chamber leukocyte infiltration was measured using a numerical scoring system to estimate cell number per field defined by a 5 mm slit width: 0=no cells per field (no response); 1=1–10 cells per field (mild); 2=11–20 cells per field (moderate); 3=26–50 cells per field (severe); 4=>50 cells per filed (florid). Results are reported as the mean score value±S.E.M.

The compounds of this invention were tested according to the method described in "Characterization of Receptor Subtypes Involved in Prostanoid-Induced Conjunctival Pruritis and Their Role in Mediating Conjunctival Itching", Vol. 279, No. 1, (JPET)279, 137-142' 1996 for their efficacy in alleviating itch. The results are reported in FIGS. 10 and 11. The results in both experiments showed a significantly lower number of itch-scratch episodes with the use of the compounds of FIGS. 3 and 3(a) thereby indicating that the compounds of this invention are useful in treating allergic conjunctivitis.

The compounds of FIGS. 3 and 3(a) were tested for mutagenicity by means of the Ames Test using Strains TA 98 and TA 100. The results were negative for both compounds.

Finally, said condition that may be treated with the compounds of this invention may be related to pain and inflammation and post-surgical scar and keloid formation.

In view of the various diseases and conditions that may be treated with the compositions of this invention there is provided a pharmaceutical product comprising a compound having the following formula:

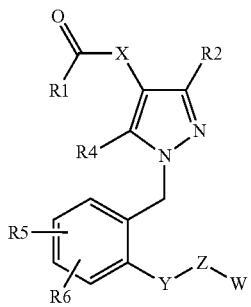

Wherein X is O, $NR_7$ or $(CH_2)_n$, wherein n is 0 or an integer of 1 or 2;

Y is $(CH_2)_m$, wherein m is 0 or an integer of from 1 to 3;

Z is selected from the group consisting of O, S, SO, $SO_2$ and $(CH_2)_p$, wherein p is 0 or an integer of from 1 to 3;

W is hydrocarbyl or substituted hydrocarbyl;

$R_1$ is selected from the group consisting of $OR_7$, $N(R_7)_2$, and $N(R_7)SO_2R_7$;

$R_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_4$ is selected from the group consisting of H, $NH_2$, alkyl, nitrogen-substituted alkyl and halogen-substituted alkyl;

$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy; and, $R_7$ is selected from the group consisting of H, hydrocarbyl and substituted hydrocarbyl, e.g. carbocyclic aryl and alkyl or a pharmaceutically acceptable salt or a prodrug thereof, wherein said product is packaged and labeled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, hyperpyrexia, gangrene, glaucoma, hypothermia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pain, perennial rhinitis, pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation.

Those skilled in the art will readily understand that for administration the compounds disclosed herein can be admixed with pharmaceutically acceptable excipients which, per se, are well known in the art. Specifically, a drug to be administered systemically, it may be formulated as a powder, pill, tablet or the like, or as a solution, emulsion, suspension, aerosol, syrup or elixir suitable for oral or parenteral administration or inhalation.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874, which are incorporated by reference in their entireties, to form osmotic therapeutic tablets for control release. Liquid pharmaceutically administrable dosage forms can, for example, comprise a solution or suspension of one or more of the compounds of the present invention and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectable formulations can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds of the present invention administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 ng/kg/day or about 1 ng/kg/day to about 100 mg/kg/day.

For ophthalmic application, solutions are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

Similarly, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

For topical use, creams, ointments, gels, solutions or suspensions, etc., containing the compound of the present invention are employed. Topical formulations may generally be comprised of a pharmaceutical carrier, cosolvent, emulsifier, penetration enhancer, preservative system, and emollient.

The actual dose of the compounds of the present invention depends on the specific compound, and on the condition to be treated; the selection of the appropriate dose is well within the knowledge of the skilled artisan.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims.

What is claimed is:

1. A compound that is a 1-[(5-halo or alkyl or fluoroalkyl or alkoxy-2-{(hydrocarbyl or substituted hydrocarbyl)oxy}phenyl)methyl]-(3 or 5 alkyl or fluoroalkyl)-1H-pyrazole-4-(carboxylic acid or methylene carboxylic acid) or an alkyl or aryl ester or sulfonamide thereof.

2. The compound of claim 1 wherein said halo is selected from the group consisting of chloro and bromo.

3. The compound of claim 1 wherein said hydrocarbyl is selected from the group consisting of alkyl and carbocyclic aryl.

4. The compound of claim 3 wherein said hydrocarbyl is selected from the group consisting of branched chain alkyl and phenyl.

5. The compound of claim 4 wherein said hydrocarbyl is selected from the group consisting of branched chain alkyl having from 4 to 7 carbons.

6. The compound of claim 1 wherein said compound is a 1-[(5-Chloro or bromo- or trifluoromethyl-2-{hydrocarbyloxy}phenyl)methyl]-(3 or 5 methyl)-1H-pyrazole-4-carboxylic acid.

7. The compound of claim 6 wherein said hydrocarbyl is selected from the group consisting of alkyl and carbocyclic aryl.

8. The compound of claim 6 wherein said hydrocarbyl is selected from the group consisting of branched chain alkyl and phenyl.

9. The compound of claim 6 wherein said hydrocarbyl a branched chain alkyl having from 4 to 7 carbons.

10. The compound of claim 1 that is selected from the group consisting of:
- 1-[(5-Bromo-2-{2-ethylbutyloxy}phenyl)methyl]-5-methyl-1H-pyrazole-4-methylenecarboxylic acid;
- 1-[(5-Bromo-2-{2-ethylbutyloxy}phenyl)methyl]-5-methyl-1H-pyrazole-4-carboxylic acid;
- 1-[(5-Bromo-2-{2-ethylbutyloxy}phenyl)methyl]-3-methyl-1H-pyrazole-4-carboxylic acid;
- 1-[(5-chloro-2-{2-ethylbutyloxy}phenyl)methyl]-1H-pyrazole-4-carboxylic acid;
- 1-[(5-Chloro-2-{2-ethylbutyloxy}phenyl)methyl]-3,5-dimethyl-1H-pyrazole-4-carboxylic acid;
- 1-[(5-chloro-2-{2-ethylbutyloxy}phenyl)methyl]-3-propyl-1H-pyrazole-4-carboxylic acid;
- 1-[(5-chloro-2-{2-ethylbutyloxy}phenyl)methyl]-5-propyl-1H-pyrazole-4-carboxylic acid;
- 1-[(5-trifluoromethyl-2-{2-ethylbutyloxy}phenyl)methyl]-5-methyl-1H-pyrazole-4-carboxylic acid;
- 1-[(5-trifluoromethyl-2-{2-ethylbutyloxy}phenyl)methyl]-3-methyl-1H-pyrazole-4-carboxylic acid;
- 1-[(5-Chloro-2-{2-ethylbutyloxy}phenyl)methyl]-5-methyl-1H-pyrazole-4-carboxylic acid;
- 1-(5-chloro-2-isobutoxy-benzyl)-5-methyl-1H-pyrazole-4-carboxylic acid;
- 1-(5-chloro-2-cyclopentylmethoxy-benzyl)-5-methyl-1H-pyrazole-4-carboxylic acid;
- 1-(5-bromo-2-isobutoxy-benzyl)-5-methyl-1H-pyrazole-4-carboxylic acid;
- 1-[5-bromo-2-(2,2-dimethyl-propoxy)-benzyl]-5-methyl-1H-pyrazole-4-carboxylic acid;
- 1-[2-(2-ethyl-butoxy)-5-trifluoromethoxy-benzyl]-5-methyl-1H-pyrazole-4-carboxylic acid; and,
- 5-amino-1-[5-bromo-2-(2-ethyl-butoxy)-benzyl]-1H-pyrazole-4-carboxylic acid.

11. A compound having the following formula:

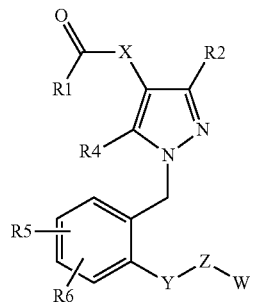

wherein:

X is O, $NR_7$ or $(CH_2)_n$, wherein n is 0 or an integer of 1 or 2;

Y is $(CH_2)_m$, wherein m is 0 or an integer of from 1 to 3;

Z is selected from the group consisting of O, S, SO, $SO_2$ and $(CH_2)_p$, wherein p is 0 or an integer of from 1 to 3;

W is hydrocarbyl or substituted hydrocarbyl;

$R_1$ is selected from the group consisting of $OR_7$, $N(R_7)_2$, and $N(R_7)SO_2R_7$;

$R_2$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_4$ is selected from the group consisting of H, $NH_2$, alkyl, nitrogen-substituted alkyl and halogen-substituted alkyl;

$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy; and, $R_7$ is selected from the group consisting of H, hydrocarbyl and substituted hydrocarbyl.

12. The compound of claim 11, wherein $R_1$ is OH.

13. The compound of claim 11, wherein $R_2$ is selected from the group consisting of H, alkyl and halogen-substituted alkyl.

14. The compound of claim 11, wherein $R_4$ is selected from the group consisting of H, alkyl and halogen-substituted alkyl.

15. The compound of claim 11, wherein $R_1$ is OH, X is $(CH_2)_n$, wherein n is 0 or 1.

16. The compound of claim 11, wherein $R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy.

17. The compound of claim 11, wherein $R_5$ is chloro or bromo.

18. The compound of claim 11, wherein $R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy.

19. The compound of claim 18, wherein $R_6$ is H.

20. The compound of claim 11, wherein Y is absent.

21. The compound of claim 11, wherein Z is O.

22. The compound of claim 11, wherein W is selected from the group consisting of alkyl, aryl, alkoxy, aryloxy and hydroxy, halogen, nitro, amino and cyano-substituted alkyl, aryl, alkoxy or aryloxy.

* * * * *

UNITED STATES PATENT AND TRADEMARK OFFICE
CERTIFICATE OF CORRECTION

PATENT NO. : 9,035,071 B2
APPLICATION NO. : 13/720488
DATED : May 19, 2015
INVENTOR(S) : Jussi J. Kangasmetsa et al.

It is certified that error appears in the above-identified patent and that said Letters Patent is hereby corrected as shown below:

On the title page, item (56), in column 2, References Cited under "Other Publications", line 4, delete "X and Y" and insert -- Z and Y --, therefor.

On the Page 2, in column 1, under "Other Publications", line 6, delete "NF-KB" and insert -- NF-κB --, therefor.

In the specification

In column 3, line 28, delete "1h" and insert -- 1H --, therefor.

In column 3, line 30, delete "1h" and insert -- 1H --, therefor.

In column 3, line 32, delete "1h" and insert -- 1H --, therefor.

In column 3, line 35, delete "1h" and insert -- 1H --, therefor.

In column 3, line 37, delete "1h" and insert -- 1H --, therefor.

In column 3, line 38, delete "1h" and insert -- 1H --, therefor.

In column 3, line 45, delete "1h" and insert -- 1H --, therefor.

In column 3, line 65, delete "nomenclature.)." and insert -- nomenclature). --, therefor.

In column 5, line 56, delete "1h" and insert -- 1H --, therefor.

In column 6, line 28, delete "(hydrocarbyl oxy)" and insert -- (hydrocarbyloxy) --, therefor.

In column 6, line 30-31, delete "(hydrocarbyl oxy)" and insert -- (hydrocarbyloxy) --, therefor.

In column 7, lines 28-29, delete "(hydrocarbyl oxy)" and insert -- (hydrocarbyloxy) --, therefor.

In column 7, line 45, delete "benzyl5-" and insert -- benzyl-5- --, therefor.

In column 8, line 1, delete "$NR_5$" and insert -- $NR_7$ --, therefor.

In column 8, line 42, delete "metastic" and insert -- metastatic --, therefor.

In column 8, lines 53-54, delete "ophthalmogical" and insert -- ophthalmological --, therefor.

In column 9, line 17, delete "alrynitis," and insert -- laryngitis, --, therefor.

In column 9, line 45, delete "sequalae" and insert -- sequelae --, therefor.

Signed and Sealed this
Twentieth Day of October, 2015

Michelle K. Lee
*Director of the United States Patent and Trademark Office*

In the specification

In column 10, line 1, delete "NR$_5$" and insert -- NR$_7$ --, therefor.

In column 10, line 38, delete "metastic" and insert -- metastatic --, therefor.

In column 10, line 65, delete "NR$_5$" and insert -- NR$_7$ --, therefor.

In column 12, line 2, delete "alkyl" and insert -- alkyl. --, therefor.

In column 13, line 11, delete "R4" and insert -- R$_4$ --, therefor.

In column 13, line 14, delete "(CH2)n," and insert -- (CH2)$_n$, --, therefor.

In column 13, line 66, delete "1-[-2-" and insert -- 1-[2- --, therefor.

In column 14, line 13, before "obtain" delete "a".

In column 14, line 25, delete "tetrahydrofurane," and insert -- tetrahydrofuran, --, therefor.

In column 15, line 20 (Approx.), delete "(10 g g" and insert -- (10 g --, therefor.

In column 15, line 32, delete "δ7.29" and insert -- δ 7.29 --, therefor.

In column 15, line 35, delete "—C(CH$_3$)$_3$)." and insert -- —C(CH$_3$)$_3$. --, therefor.

In column 15, line 48, delete "yl]acetic" and insert -- yl]-acetic --, therefor.

In column 15, line 67, delete "1 1 g" and insert -- 11 g --, therefor.

In column 16, line 50, delete "(0.18 g g" and insert -- (0.18 g --, therefor.

In column 16, line 62, delete "1H" and insert -- 1H, --, therefor.

In column 16, line 62, delete "(4," and insert -- (d, --, therefor.

In column 16, line 64, delete "ArCH$_2$),)," and insert -- ArCH$_2$), --, therefor.

In column 17, line 38, delete "(," and insert -- (s, --, therefor.

In column 18, line 22, delete "1 2 g" and insert -- 12 g --, therefor.

In column 21, line 63, delete "1H-NMR," and insert -- $^1$H-NMR, --, therefor.

In column 21, line 63, delete "1H ArCHO,)," and insert -- 1H, ArCHO), --, therefor.

In column 21, line 64, delete "ArH,)," and insert -- ArH), --, therefor.

In column 22, line 3, delete "phenyl]methanol," and insert -- phenyl]-methanol, --, therefor.

In column 22, line 27, delete "ArH,)," and insert -- ArH), --, therefor.

In column 22, line 61, delete "(0.3 g g" and insert -- (0.3 g --, therefor.

In column 23, line 1, delete "ArH,)," and insert -- ArH), --, therefor.

In column 23, line 45, after "CH$_3$)." delete "LC-MS: m/z 365 M+H$^+$." and insert the same on, in column 24, line 46, as a new Paragraph.

In column 25, line 2, after "CH$_3$)." delete "LC-MS: m/z 393 M+H$^+$." and insert the same on, in column 25, line 3, as a new Paragraph.

In column 28, line 26, delete "ArH,)," and insert -- ArH), --, therefor.

In column 29, line 34, delete "regio isomer." and insert -- regioisomer. --, therefor.

In column 32, line 40, delete "1" and insert -- 1H --, therefor.

CERTIFICATE OF CORRECTION (continued)
U.S. Pat. No. 9,035,071 B2

In the specification

In column 32, line 61, delete "reagents" and insert -- reagents. --, therefor.

In column 33, line 26, delete "reagents" and insert -- reagents. --, therefor.

In column 36, line 1, delete "1h" and insert -- 1H --, therefor.

In column 36, line 33, delete "1h" and insert -- 1H --, therefor.

In column 36, line 53, delete "Step 4" and insert -- Step 4. --, therefor.

In column 37, line 3, delete "haemagglutanin" and insert -- haemagglutinin --, therefor.

In column 37, line 22, delete "$Ca^{2-}$" and insert -- $Ca^{2+}$ --, therefor.

In column 39, line 36, delete "metastic" and insert -- metastatic --, therefor.

In column 39, line 48, delete "ophthalmogical" and insert -- ophthalmological --, therefor.

In column 39, line 67, delete "alrynitis," and insert -- laryngitis, --, therefor.

In column 40, line 16, delete "sequalae" and insert -- sequelae --, therefor.

In column 41, line 8, delete "and or" and insert -- and/or --, therefor.

In column 42, line 56, delete "Pruritis" and insert -- Pruritus --, therefor.

In column 42, line 58, delete "(JPET)279," and insert -- (JPET) 279, --, therefor.

In column 43, line 60, delete "metastic" and insert -- metastatic --, therefor.

In the claims

In column 46, line 11, in claim 9, after "hydrocarbyl" insert -- is --.